United States Patent
Li et al.

(10) Patent No.: US 8,007,790 B2
(45) Date of Patent: Aug. 30, 2011

(54) METHODS FOR TREATING POLYCYSTIC KIDNEY DISEASE (PKD) OR OTHER CYST FORMING DISEASES

(75) Inventors: Rong Li, Kansas City, MO (US); Xiaogang Li, Prairie Village, KS (US)

(73) Assignee: Stowers Institute for Medical Research, Kansas City, MO (US)

( * ) Notice: Subject to any disclaimer, the term of this patent is extended or adjusted under 35 U.S.C. 154(b) by 469 days.

(21) Appl. No.: 11/906,600

(22) Filed: Oct. 2, 2007

(65) Prior Publication Data

US 2008/0269123 A1 Oct. 30, 2008

Related U.S. Application Data

(63) Continuation-in-part of application No. PCT/US2007/065869, filed on Apr. 3, 2007.

(60) Provisional application No. 60/744,182, filed on Apr. 3, 2006, provisional application No. 60/825,873, filed on Sep. 15, 2006.

(51) Int. Cl.
 *A61K 39/395* (2006.01)
 *A61K 39/00* (2006.01)
 *A61K 38/00* (2006.01)
 *C07K 16/24* (2006.01)

(52) U.S. Cl. ............... 424/130.1; 424/133.1; 424/135.1; 424/141.1; 424/145.1; 514/1.1

(58) Field of Classification Search .................. None
 See application file for complete search history.

(56) References Cited

U.S. PATENT DOCUMENTS

| | | | |
|---|---|---|---|
| 4,508,703 A | 4/1985 | Redziniak et al. | |
| 4,621,023 A | 11/1986 | Redziniak et al. | |
| 5,034,506 A | 7/1991 | Summerton et al. | |
| 5,077,211 A | 12/1991 | Yarosh | |
| 5,235,033 A | 8/1993 | Summerton et al. | |
| 5,270,163 A | 12/1993 | Gold et al. | |
| 5,395,760 A | 3/1995 | Smith et al. | |
| 5,605,690 A | 2/1997 | Jacobs et al. | |
| 5,750,495 A | 5/1998 | Woo | |
| 5,945,397 A | 8/1999 | Smith et al. | |
| 5,981,701 A | 11/1999 | Wallach et al. | |
| 6,015,557 A | 1/2000 | Tobinick et al. | |
| RE36,755 E | 6/2000 | Smith et al. | |
| 6,271,346 B1 | 8/2001 | Hauptmann et al. | |
| 6,291,646 B1 | 9/2001 | Sledziewski et al. | |
| 6,358,508 B1 | 3/2002 | Ni et al. | |
| 6,379,666 B1 | 4/2002 | Tobinick | |
| 6,419,934 B1 | 7/2002 | Tobinick | |
| 6,419,944 B2 | 7/2002 | Tobinick | |
| 6,423,321 B2 | 7/2002 | Tobinick | |
| 6,428,787 B1 | 8/2002 | Tobinick | |
| 6,455,040 B1 | 9/2002 | Wei et al. | |
| 6,503,184 B1 | 1/2003 | Ni et al. | |
| 6,537,549 B2 | 3/2003 | Tobinick | |
| 6,541,224 B2 | 4/2003 | Yu et al. | |
| 6,638,726 B1 | 10/2003 | Wilson et al. | |
| 6,689,607 B2 | 2/2004 | Ni et al. | |
| 7,226,593 B2 | 6/2007 | Le et al. | |
| 2001/0021380 A1* | 9/2001 | Pluenneke | .................. 424/131.1 |
| 2002/0115080 A1 | 8/2002 | Skouv et al. | |
| 2003/0148264 A1 | 8/2003 | Held et al. | |
| 2005/0107325 A1 | 5/2005 | Manoharan et al. | |
| 2005/0182005 A1 | 8/2005 | Tuschl et al. | |
| 2005/0196817 A1 | 9/2005 | Kingsmore et al. | |
| 2005/0267135 A1 | 12/2005 | Escardo et al. | |
| 2005/0282909 A1 | 12/2005 | Diks et al. | |
| 2006/0046961 A1 | 3/2006 | McKay et al. | |
| 2006/0182716 A1 | 8/2006 | Hong et al. | |
| 2006/0275823 A1 | 12/2006 | Kodadek | |
| 2007/0065447 A1 | 3/2007 | Tryggvason et al. | |
| 2007/0259352 A1 | 11/2007 | Bentwich et al. | |
| 2008/0182237 A1 | 7/2008 | Bentwich et al. | |

FOREIGN PATENT DOCUMENTS

| | | |
|---|---|---|
| WO | WO 91/03553 | 3/1991 |
| WO | WO 94/06476 | 3/1994 |
| WO | WO 03/048108 | 6/2003 |
| WO | WO 2005/116250 | 12/2005 |
| WO | WO 2006/126040 | 11/2006 |

OTHER PUBLICATIONS

Biomed Valley Discoveries, Polycystic Kidney Disease, Enbrel Repurposing Project, pp. 1-13 (2010).
Bhunia et al., "PKD1 Induces p21waf1 and Regulation of the Cell Cycle Via Direct Activation of the JAK-STAT Signaling Pathway in a Process Requiring PKD2," Cell, vol. 109, pp. 157-168 (2002).
Li et al., "Polycystin-1 and Polycystin-2 Regulate the Cell Cycle Through the Helix-Loop-Helix Inhibitor Id2," Nature Cell Biology, vol. 7, No. 12, pp. 1102-1112 (2005).
Nagao et al., "Renal Activation of Extracellular Signal-Regulated Kinase in Rats With Autosomal-Dominant Polycystic Kidney Disease," Kidney Int., vol. 63, pp. 427-437 (2003).
Nauli et al., "Polycystins 1 and 2 Mediate Mechanosensation in the Primary Cilium of Kidney Cells," Nature Genetics, vol. 33, pp. 129-137 (2003).
Wilson et al., "Cystic Disease of the Kidney," Annu. Rev. Pathol., vol. 2, pp. 341-368 (2007).

(Continued)

Primary Examiner — Christine J Saoud
Assistant Examiner — Jon M Lockard
(74) Attorney, Agent, or Firm — Bryan Cave LLP

(57) ABSTRACT

The present invention is directed to methods of treating or ameliorating an effect of a polycystic disease. More particularly, the methods include administering to a patient in need thereof an amount of a modulator of a tumor necrosis factor (TNF) pathway, which is sufficient to treat or ameliorate an effect of a polycystic disease. Methods of treating or ameliorating an effect of a polycystic kidney disease (PKD) are also provided. Methods are also provided for identifying a candidate compound that may be effective to treat or ameliorate an effect of a polycystic disease or to increase polycystin-2 (PC2) function or decrease Rab11-Family of Interacting Protein2 (FIP2) function. Further provided are methods for identifying a patient having, or who is at risk for developing, a polycystic disease or who would benefit from treatment with a TNF-alpha inhibitor.

7 Claims, 7 Drawing Sheets
(7 of 7 Drawing Sheet(s) Filed in Color)

OTHER PUBLICATIONS

Aguiari et al., "Deficiency of Polycystin-2 Reduces Ca2+ Channel Activity and Cell Proliferation in ADPKD Lymphoblastoid Cells," FASB J., vol. 18, pp. 884-886 (2004).

Blind et al., "Cytoplasmic RNA Modulators of an Inside-Out Signal-Transduction Cascade," Proc. Natl. Acad. Sci. USA, vol. 96, pp. 3606-3610 (1999).

Brody et al., "Aptamers As Therapeutic and Diagnostic Agents," Reviews in Molecular Biotechnology, vol. 74, pp. 5-13 (2000).

Bugg et al., "Drugs by Design: Structure-Based Design, An Innovative Approach to Developing Drugs, Has Recently Spawned Many Promising Therapeutic Agents, Including Several Now in Human Trials for Treating AIDS, Cancer and Other Diseases," Sci. Am., vol. 269, pp. 92-98 (1993).

Burger et al., "Drug Screening Using Cell Lines: Cell Supply, High-Throughput and High-Content Assays," Drug Testing in Vitro: Breakthroughs and Trends in Cell Culture Technology, Marx and Sandig eds., Wiley-VCH, Chapter 5, pp. 127-151 (2007).

Cano et al., "orpk Mouse Model of Polycystic Kidney Disease Reveals Essential Role of Primary Cilia in Pancreatic Tissue Organization," Development and Disease, vol. 131, pp. 3457-3467 (2004).

Casset et al., "A Peptide Mimetic of an Anti-CD4 Monoclonal Antibody by Rational Design," Biochem. Biophys. Res. Commun., vol. 307(1), pp. 198-205 (2003).

Chauvet et al., "Expression of PKD1 and PKD2 Transcripts and Proteins in Human Embryo and During Normal Kidney Development," Am. J. Pathol., vol. 160(3), pp. 973-983 (2002).

Cohen et al., "Structure Design: an Artificial Intelligence-Based Method for the Design of Molecules Under Geometrical Constraints," J. Mol. Graphics, vol. 11, pp. 166-173 (1993).

Cortez-Retamozo et al., "Efficient Cancer Therapy With a Nanobody-Based Conjugate," Cancer Res., vol. 64(8), pp. 2853-2857 (2004).

Dean, "Recent Advances in Drug Design Methods: Where Will They Lead?" BioEssays, vol. 16, No. 9, pp. 683-687 (1994).

Enjalbal et al., "Mass Spectrometry in Combinatorial Chemistry," Mass Spectrom. Rev., vol. 19, pp. 139-161 (2000).

Fassina, "Complementary Peptides As Antibody Mimetics for Protein Purification and Assay," Immunomethods, vol. 5(2), pp. 121-129 (1994).

Fischer et al., "Protection by Phosphodiesterase Inhibitors Against Endotoxin-Induced Liver Injury in Galactosamine-Sensitized Mice," Biochem. Pharmacol., vol. 45, No. 12, pp. 2399-2404 (1993).

Gantner et al., "Protection From T Cell-Mediated Murine Liver Failure by Phosphodiesterase Inhibitors," J. Pharmacol. Exp. Ther., vol. 280, pp. 53-60 (1997).

Genain et al., "Prevention of Autoimmune Demyelination in Non-Human Primates by a cAMP-Specific Phosphodiesterase Inhibitor," Proc. Natl. Acad. Sci. USA, vol. 92, pp. 3601-3605 (1995).

Hruby, "Conformational and Topographical Considerations in the Design of Biologically Active Peptides," Biopolymers, vol. 33, pp. 1073-1082 (1993).

Ibraghimov-Beskrovnaya et al., "Polycystin: in Vitro Synthesis, in Vivo Tissue Expression, and Subcellular Localization Identifies a Large Membrane-Associated Protein," Proc. Natl. Acad. Sci. USA, vol. 94, pp. 6397-6402 (1997).

Krutzfeld et al., "Silencing of MicroRNAs in Vivo With 'Antagomirs'," Nature, vol. 438, pp. 685-689 (2005).

Kumar et al., "p38 MAP Kinases: Key Signaling Molecules As Therapeutic Targets for Inflammatory Diseases," Nat. Rev. Drug Discov., vol. 2(9), pp. 717-726 (2003).

Lee et al., A Protein Kinase Involved in the Regulation of Inflammatory Cytokine Biosynthesis, Nature, vol. 372(6508), pp. 739-746 (1994).

Markowitz et al., "Polycystin-2 Expression Is Developmentally Regulated," Am. J. Physiol., vol. 277 (1 Pt. 2), pp. F17-F25 (1999).

Marx et al., "Modulation of TNF and GM-CSF Release From Dispersed Human Nasal Polyp Cells and Human Whole Blood by Inhibitors of Different PDE Isoenzymes and Glucocorticoids," Pul. Pharmacol. & Ther., vol. 15, pp. 7-15 (2002).

Miwatashi et al., "Novel Inhibitor of p38 MAP Kinase As an Anti-TNF-alpha Drug: Discovery of N-[4 [2-Ethyl-4(3-methylphenyl)-1,3-thiazol-5-yl]-2-pyridyl]benzamide (TAK-715) As a Potent and Orally Active Anti-Rheumatoid Arthritis Agent," J. Med. Chem., vol. 48, No. 19, pp. 5966-5979 (2005).

Moore, "Designing Peptide Mimetics," TiPS, vol. 15, pp. 124-129 (1994).

Morjaria et al., "Impairment of TNF-alpha Production and Action by Imidazo[1,2-alpha] Quinoxalines, a Derivative Family Which Displays Potential Anti-Inflammatory Properties," Int. J. Immunopathol. Pharmacol., vol. 19, No. 3, pp. 525-538 (2006).

Palladino et al., "Anti-TNF-alpha Therapies: the Next Generation," Nature, vol. 2, pp. 736-746 (2003).

Peifer et al., "New Approaches to the Treatment of Inflammatory Disorders Small Molecule Inhibitors of p38 MAP Kinase," Current Topics in Medical Chemistry, vol. 6, No. 2, pp. 113-149 (2006).

Prabhakar et al., "Characterization of cAMP-Dependent Inhibition of LPS-Induced TNF-alpha Production by Rolipram, A Specific Phosphodiesterase IV (PDE IV) Inhibitor," Int. J. Immunopharmac., vol. 16, No. 10, pp. 805-816 (1994).

Saklatvala, "The p38 MAP Kinase Pathway As a Therapeutic Target in Inflammatory Disease," Curr. Opin. Pharmacol., vol. 4(4), pp. 372-377 (2004).

Saragovi et al., "Design and Synthesis of a Mimetic From an Antibody Complementarity-Determining Region," Science, vol. 253(5021), pp. 792-795 (1991).

Schade et al., "The Specific Type III and IV Phosphodiesterase Inhibitor Zardaverine Suppresses Formation of Tumor Necrosis Factor by Macrophages," Eur. J. Pharmacol., vol. 230, pp. 9-14 (1993).

Schudt et al., "Effect of Selective Phosphodiesterase (PDE) Inhibitors on Activation of Human Macrophages and Lymphocytes," Eur. Res. J., vol. 6(Suppl. 17), pp. 367s-367s (1993).

Schudt et al., "PDE Isoenzymes As Targets for Anti-Asthma Drugs," Eur. Respir. J., vol. 8, pp. 1179-1183 (1995).

Seldon et al., "Suppression of Lipopolysaccharide-Induced Tumor Necrosis Factor-alpha Generation From Human Peripheral Blood Monocytes by Inhibitors of Phosphodiesterase 4: Interaction With Stimulants of Adenylyl Cyclase," Mol. Pharmacol., vol. 48, pp. 747-757 (1995).

Semmler et al., "The Specific Type IV Phosphodiesterase Inhibitor Rolipram Suppresses Tumor Necrosis Factor-alpha Production by Human Mononuclear Cells," Int. J. Immunopharmac., vol. 15, No. 3, pp. 409-413 (1993).

Skerra, "'Anticalins': A New Class of Engineered Ligand-Binding Proteins With Antibody-Like Properties," Reviews in Molecular Biotechnology, vol. 74, pp. 257-275 (2001).

Sommer et al., "The Antidepressant Rolipram Suppresses Cytokine Production and Prevents Autoimmune Encephalomyelitis," Nature Med., vol. 1, No. 3, pp. 244-248 (1995).

Soutchek et al., "Therapeutic Silencing of an Endogenous Gene by Systemic Administration of Modified siRNAs," Nature, vol. 432, pp. 173-178 (2004).

Stokely et al., "Polycystin-1 Can Interact With Homer 1/Ves1-1 in Postnatal Hippocampal Neurons," J. Neurosci. Res., vol. 84(8), pp. 1727-1737 (2006).

Torres et al., "Vascular Expression of Polycystin-2," J. Am. Soc. Nephrol., vol. 12, pp. 1-9 (2001).

Turteltaub et al., "Bioanalytical Applications of Accelerator Mass Spectrometry for Pharmaceutical Research," Curr. Pharm. Des., vol. 6, No. 10, pp. 991-1007 (2000).

Wagner et al., "Small Molecular Anti-Cytokine Agents," Medicinal Research Reviews, vol. 26, No. 1, pp. 1-62 (2006).

Weiss et al., "Anticalins Versus Antibodies: Made-To-Order Binding Proteins for Small Molecules," Chem. Biol., vol. 7, No. 8, pp. R177-R184 (2000).

Wiley et al., "Peptidomimetics Derived From Natural Products," Med. Res. Rev., vol. 13, No. 3, pp. 327-384 (1993).

Xiao et al., "Cilia-Like Structures and Polycystin-1 in Osteoblasts/Osteocytes and Associated Abnormalities in Skeletogenesis and Runx2 Expression," J. Biol. Chem., vol. 281, No. 41, pp. 30884-30895 (2006).

Li et al., "Polycystin-1 and Polycystin-2 Regulate The Cell Cycle Through the Helix-Loop-Helix Inhibitor Id2," Nature Cell Biology, vol. 7(12), pp. 1202-1212 (2005).

Manderson et al., "Subcompartments Of the Macrophage Recycling Endosome Direct the Differential Secretion of IL-6 and TNFβ," J Cell Biol., vol. 178(1), pp. 57-69 (2007).

Bhalal et al., "Molecular Basis of Autosomal Dominant Polycystic Kidney Disease," Adv. Anat. Pathol., vol. 12(3), pp. 126-133 (2005).

Dell et al., "A Novel Inhibitor of Tumor Necrosis Factor-Alpha Converting Enzyme Ameliorates Polycystic Kidney Disease," Kidney International, vol. 60, pp. 1240-1248 (2001).

Wagner et al., "Small Molecular Anti-Cytokine Agents," Medicinal Research Reviews, vol. 26(1), pp. 1-62 (2006).

Wahl et al., "Inhibition of mTOR With Sirolimus Slows Disease Progression in Han:SPRD Rats With Autosomal Dominant Polycystic Kidney Disease (ADPKD)," Nephrol. Dial. Transplant., vol. 21, pp. 598-604 (2006).

Nemo et al., "Transforming Growth Factor Alpha (TGF-α) and Other Targets of Tumor Necrosis Factor-Alpha Converting Enzyme (TACE) in Murine Polycystic Kidney Disease," Pediatric Research, 57:732-737 (2005).

Pruessmeyer et al., "The Good, the Bad and the Ugly Substrates for ADAM10 and ADAM17 in Brain Pathology, Inflammation and Cancer," Seminars in Cell & Dev. Bio., 20:164-174 (2009).

* cited by examiner

METHODS FOR TREATING POLYCYSTIC KIDNEY DISEASE (PKD) OR OTHER CYST FORMING DISEASES

CROSS-REFERENCE TO RELATED APPLICATIONS

This application is a continuation-in-part of International Patent Application No. PCT/US2007/065869, filed Apr. 3, 2007, which claims the benefit of U.S. Provisional Application No. 60/744,182, filed Apr. 3, 2006, and U.S. Provisional Application No. 60/825,873, filed Sep. 15, 2006, the contents of which are incorporated herein by reference.

FIELD OF INVENTION

The present invention relates to methods for treating or ameliorating the effects of a polycystic disease, such as for example, polycystic kidney disease (PKD). The present invention also relates to screening methods for identifying candidate compounds that may be effective to treat or ameliorate a polycystic disease, to increase polycystin-2 function or decrease Rab11-Family of Interacting Protein2 function (Optineurin or FIP2). The present invention also relates to methods of identifying a patient having, or who is at risk for developing, a polycystic disease or who would benefit from treatment with a TNF-alpha inhibitor.

BACKGROUND OF INVENTION

Polycystic kidney disease (PKD) is a common inherited human nephropathy that affects approximately 1:1000 of the worldwide population and is the third-most common cause of end stage renal failure. Renal cysts progressively develop in patients afflicted with PKD, and are associated with complications such as cyst infection and hemorrhage, renal stones, and pain. PKD largely results from the Autosomal Dominant Polycystic Kidney Disease (ADPKD), which is attributed to heterozygous mutations in either the Pkd1 or Pkd2 gene. These genes respectively encode the large, membrane-associated proteins Polycystin-1 (PC1) and Polycystin-2 (PC2). In PKD, cyst formation and the associated symptoms may be caused by loss of polycystin function.

No effective treatment for PKD or other cyst-forming disease is currently known. Previous unsuccessful attempts at treatment have included increasing the levels of Tissue Necrosis Factor-alpha (TNF-alpha) in a patient. Accordingly, there exists, inter alia, a need for treating and/or ameliorating the symptoms of PKD and other cyst-forming diseases.

SUMMARY OF INVENTION

The present invention is directed, inter alia, to treating and/or ameliorating the effects of PKD and related conditions by regulating TNF pathway modulators. Related methods and screening assays are also provided.

In one embodiment, there is provided a method of treating or ameliorating an effect of a polycystic disease. This method comprises administering to a patient in need thereof an amount of a modulator of a tumor necrosis factor (TNF) pathway, which is sufficient to treat or ameliorate an effect of a polycystic disease.

Another embodiment of the invention is a method of treating or ameliorating an effect of a polycystic kidney disease (PKD). This method comprises administering to a patient in need thereof an amount of a TNF-alpha inhibitor that is sufficient to treat or ameliorate an effect of PKD.

A further embodiment of the invention is a method for identifying a candidate compound that may be effective to treat or ameliorate an effect of a polycystic disease or to increase polycystin-2 (PC2) function or decrease Rab11-Family of Interacting Protein2 (FIP2) function. This method comprises (a) contacting a test cell that expresses PC2 with an amount of a TNF-alpha pathway modulator, which is effective to modulate FIP2 expression in the test cell and/or to disrupt PC2 localization or function at a plasma membrane or a primary cilia of the test cell, (b) further contacting the test cell from step (a) with a candidate compound, and (c) determining whether the candidate compound increases PC2 localization to the plasma membrane of the test cell, the primary cilia of the test cell, or both or increases PC2 function or decreases FIP2 expression in the test cell compared to a control cell treated in an identical fashion except that it was not contacted with the candidate compound. A candidate compound that increases PC2 localization to the plasma membrane of the test cell, the primary cilia of the test cell, or both or increases PC2 function or decreases FIP2 expression in the test cell relative to the control cell is indicative that the candidate compound may be effective to treat or ameliorate the effects of a polycystic disease or to increase PC2 function or FIP2 expression.

Another embodiment of the invention is a method for identifying a patient having, or who is at risk for developing, a polycystic disease. This method comprises determining whether a patient has an elevated level of TNF-alpha, FIP2, or both, compared to control levels of TNF-alpha, FIP2, or both in a patient population that does not have the polycystic disease. A patient that has an elevated level of TNF-alpha, FIP2, or both compared to the control has, or is at risk of developing, a polycystic disease.

A further embodiment of the invention is a method for identifying a patient who may benefit from treatment with a TNF-alpha inhibitor. This method comprises determining whether a patient has an elevated level of TNF-alpha, FIP2, or both, compared to control levels of TNF-alpha, FIP2, or both in a patient population that does not have the polycystic disease. A patient that has an elevated level of TNF-alpha, FIP2, or both compared to the control may benefit from treatment with a TNF-alpha inhibitor.

These and other aspects of the invention are further disclosed in the detailed description and examples which follow.

BRIEF DESCRIPTION OF DRAWINGS

The application contains at least one drawing executed in color. Copies of this patent and/or application publication with color drawing(s) will be provided by the Office upon request and payment of the necessary fee. The following drawings form part of the present specification and are included to further demonstrate certain aspects of the present invention. The invention may be better understood by reference to one or more of these drawings in combination with the Detailed Description and the Examples presented herein.

FIG. 7a shows transfected IMCD cells with 4 different siRNA against FIP2 showing diminished FIP2 expression. siRNA#08 (SEQ ID NO: 8) had the strongest effect. FIG. 7b shows a Western blot to determine the FIP2 levels in IMCD cells which were transfected with siRNA#05 (SEQ ID NO: 2) and #08 (SEQ ID NO: 8) and then treated with TNF-alpha for 16 hours. FIGS. 7c and 7d show immunostaining with 96525 anti-PC2 antibody of the IMCD cells transfected with siRNA#08 (SEQ ID NO: 8) before and after TNF-alpha induction indicating that the siRNA rescued the TNF-alpha effect on PC2 localization. FIGS. 7e and 7f show immunostaining with YCC2 anti-PC2 antibody of the IMCD cells transfected with siRNA#08 (SEQ ID NO: 8) before and after TNF-alpha induction demonstrating that the siRNA rescued the PC2 cilia localization even treated with TNF-alpha effect.

DETAILED DESCRIPTION

Figure 1:
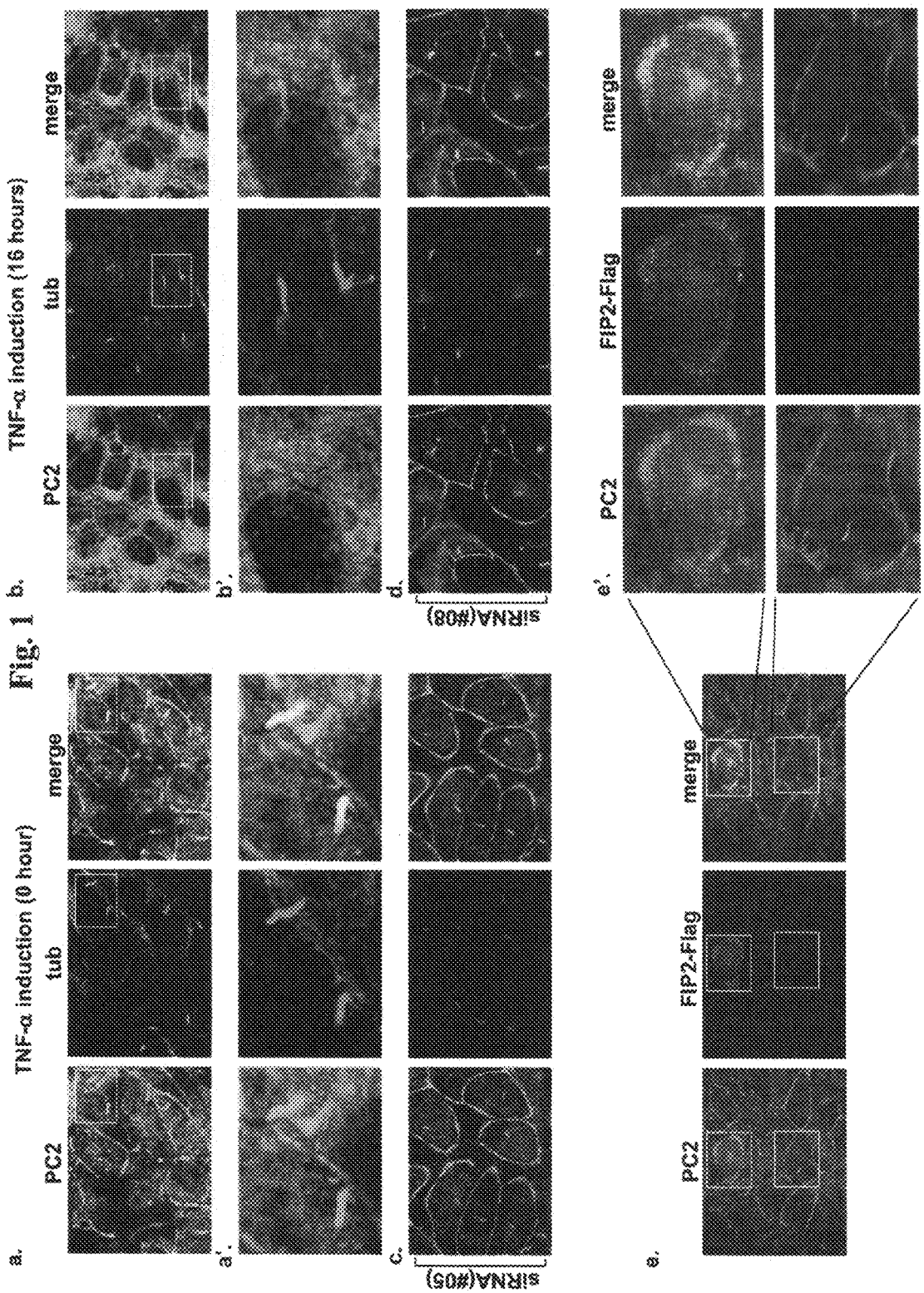
FIG. 1a-e' is a series of photographs, which show that TNF-alpha signaling disrupts PC2 localization in Inner Medullary Collecting Duct (IMCD) cells.

The inventors have made the surprising discovery that modulators of the TNF pathway, e.g., the TNF-alpha pathway, may be used to treat polycystic disease, particularly PKD, such as ADPKD. This is based on the unexpected observation that TNF-alpha, an inflammatory cytokine present in cystic fluid, disrupts localization of PC2 to the plasma membrane and primary cilia through a scaffold protein, FIP2, which is induced by TNF-alpha. While not bound by theory, the induction of FIP2 expression by TNF-alpha, disrupts the localization of PC2 to the plasma membrane and primary cilia. As a result of the increased levels of FIP2, PC1 and PC2 interaction and localization to the plasma membrane are inhibited thereby disrupting the formation of transmembrane complexes. A lack of PC1 and PC2 interaction may lead to an increase in cell proliferation, a decrease in cell differentiation, and cyst formation in organs such as the kidney. In contrast, if FIP2 expression is decreased or inhibited, this may promote the formation of transmembrane complexes between PC1 and PC2, whereby PC2 remains localized to the plasma membrane of the cell and cells differentiate without increased levels of proliferation.

TNF-alpha inhibitors and other modulators of the TNF pathway directly or indirectly regulate FIP2 expression. These insights lead to use of other related TNF-alpha inhibitory agents to treat other diseases affected by FIP2 overexpression and polycystin dysfunction. Other aspects of the invention will become apparent to the skilled artisan by the following description of the invention.

1. Definitions

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Cancer

"Cancer" as used herein may mean the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma) esophagus, stomach, gall bladder, cervix, thyroid, renal, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoeietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

b. Derivative

"Derivative" as used herein may mean a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives may include fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

c. Fragment

"Fragment" as used herein when used in the context of a peptide or polypeptide, may mean a peptide of from about 5 to about 150, about 6 to about 100, or about 8 to about 50 amino acids in length.

d. Rab11-Family of Interacting Protein2 (Optineurin or FIP2)

In the present invention, "Rab11-Family of Interacting Protein2", "FIP2", and "Optineurin" are used interchangeably to refer to a TNF-alpha inducible coiled-coiled protein that may be functioning in PC2 expressing cells as an adaptor protein involved in vesicular trafficking. In the present invention, a "FIP2 inhibitor" is any agent that results in decreased expression or function of a FIP2 polypeptide. Representative, non-limiting examples of a FIP2 inhibitor include nucleic acids, polypeptides, polysaccharides, small organic or inorganic molecules, and combinations thereof. Preferably, the FIP2 inhibitor may be a fusion protein, including a receptor trap, an antibody, antibody mimetic, domain antibody, targeted aptamer, RNAi, siRNA, shRNA, antisense sequence, small molecule, and polysaccharide. More preferably, the FIP2 inhibitor is a siRNA comprising a nucleotide sequence selected from SEQ ID NOs: 2, 4, 6, 8, and combinations thereof.

e. High Throughput Screen

The phrase "High Throughput Screen" (HTS) as used herein defines a process in which large numbers of candidate compounds are tested rapidly and in parallel for binding activity or biological activity against target molecules. In the HTS, the candidate compounds may act as, for example but not limited to, inhibitors of target enzymes, as competitors for binding of a natural ligand to its receptor, or as agonists/antagonists for receptor-mediated intracellular processes. In certain embodiments, large number of compounds may be for example more than 100 or more than 300 or more than 500 or more than 1,000 compounds. Preferably, the process is an automated process. HTS is a known method of screening to those skilled in the art.

f. Modulator of a Tumor Necrosis Factor (TNF) Pathway

As used herein, "a modulator of a Tumor Necrosis Factor Pathway" (or "TNF pathway modulator") is any agent that regulates the activity of any member of the TNF pathway, which results in, e.g., decreased FIP2 expression in a PC2 expressing cell, and/or increased PC2 function in a PC2 expressing cell, and/or increased PC2 localization to a plasma membrane or to a primary cilia of a PC2 expressing cell. A modulator of the TNF pathway may act upstream or downstream of TNF-alpha.

Representative, non-limiting examples of members of a TNF pathway, such as a TNF-alpha pathway, include tissue necrosis factor (TNF)-alpha, TNF-alpha receptor, tissue necrosis factor receptor-1 (TNFR1), tissue necrosis factor receptor-2 (TNFR2), Fas-associated death domain protein (FADD), Rab11-Family of Interacting Protein2 (FIP2), TNF-receptor-associated death domain protein (TRADD), receptor-interacting protein-1 (RIP-1), TNF receptor-associated factors (TRAFs), phosphodiesterase IV (PDE4), p38 mitogen activated protein (MAP) kinase, fibrocystin, or a TNF-alpha-associated polypeptide. In the present invention, "TRAFs" mean all TNF receptor associated factors that are members of a TNF pathway, particularly the TNF-alpha pathway, such as for example, TRAF2 and TRAF5. In the present invention, multiple TNF pathway modulators may be used.

Preferably the modulator of the TNF pathway is a TNF-alpha inhibitor. In the present invention, the TNF-alpha inhibitor may be selected from the following classes of agents: nucleic acids, polypeptides, polysaccharides, small organic or inorganic molecules, and combinations thereof. Preferably, the TNF-alpha inhibitor may be a fusion protein, including a receptor trap, an antibody, antibody mimetic, domain antibody, targeted aptamer, RNAi, siRNA, shRNA, antisense sequence, small molecule, and polysaccharide.

Representative, non-limiting examples of TNF-alpha inhibitors according to the present invention include: Cyto-Fab (a polyclonal ovine anti TNF-alpha-antibody Fab fragment), certolizumab pegol (a PEGylated Fab'TM fragment of a humanized anti-TNF-alpha monoclonal antibody), IP-751 (a synthetic cannabinoid), adalimumab (a recombinant human IgG$_1$ monoclonal anti TNF-alpha antibody), etanercept (a dimeric fusion protein consisting of the extracellular ligand-binding domain of the human 75 kd (p75) TNF receptor linked to the Fc portion of human IgG$_1$), lenalidomide (a thalidomide analog, 3-(4-amino-1-oxo 1,3-dihydro-2H-isoindol-2-yl)piperidine-2,6-dione), ITF-2357 (a hydroxamic acid linked to an aromatic ring), infliximab (a human-mouse chimeric IgG$_1$κ anti-TNF-alpha monoclonal antibody), talactoferrin alfa (a recombinant human lactoferrin), pirfenidone (5-methyl-1-phenyl-2-(1H)-pyridone), simvastatin (butanoic acid, 2,2-dimethyl-, 1,2,3,7,8,8a-hexahydro-3,7-dimethyl-8-[2-(tetrahydro-4-hydroxy-6-oxo-2H-pyran-2-yl)-ethyl]-1-naphthalenyl ester, [1S-[1α,3α,7β,8β (2S*,4S*),-8aβ]]), onercept (a recombinant human soluble p55 TNF binding protein), tacrolimus ([3S-[3R*[E(1S*,3S*, 4S*)],4S*,5R*,8S*,9E,12R*,14R*,15S*,16R*,18S*,19S*, 26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4, 10,12,18-tetramethyl-8-(2-propenyl)-15,19-epoxy-3H-pyrido[2,1-c][1,4]oxaazacyclotricosine-1,7,20,21(4H,23H)-tetrone, monohydrate), thalidomide (α-(N-phthalimido) glutarimide), dersalazine (an azo derivative of a PAF antagonist and a 5-ASA with anti-TNFa activity), tgAAC94 (a recombinant adeno-associated virus serotype 2 (AAV2) vector genetically engineered to contain the cDNA for a human tumor necrosis factor receptor (TNFR)-immunoglobulin (IgG1) Fc fusion (TNFR:Fc) gene), Genz-29155 (a small molecule TNF-alpha inhibitor), pomalidomide (4-amino-2-[(3RS)-2,6-dioxopiperidin-3-yl]-1H-isoindole-1,3(2H)-dione), VT-346 (a 43-kd secreted glycoprotein that is a human TNF-alpha inhibitor), UR-1505 (2-Hydroxy-4(-2,2, 3,3,3-pentafluoropropoxy)-benzoic acid), PMI-001 (an extract from the roots of a perennial shrub), ENMD-1420 (a synthetic diaryl compound), golimumab (a fully human anti-TNF-alpha antibody), CYT-6091 (a nanotherapeutic in which TNF-alpha is covalently linked onto the surface of 30 nm particles of pegylated colloidal gold), Dom-0200 (an anti-TNF-alpha human domain antibody), ABX/0401 (a sc humanized anti-TNF-alpha monoclonal antibody), XPro-1595 (a dominant negative protein variant of TNF-alpha that selectively inhibits soluble TNF-alpha), anti-TNF-alpha, Borean (a C-type lectin domain (CTLD)-derived trimeric TNF-alpha antagonist), ABX/0402 (a humanized anti-TNF-alpha monoclonal antibody), TNF-alpha kinoid (a kinoid vaccine, which induces synthesis of polyclonal antibodies against TNF-alpha), CC-11006 (a class II thalidomide analog), apremilast ((+)-N-[2-[(1S)-1-(3-ethoxy-4-methoxyphenyl)-2-(methylsulfonyl)ethyl]-1,3-dioxo-2,3-dihydro-1H-isoindol-4-yl]acetamide), CC-11050 (an orally active selective cytokine inhibitory drug), YSIL6 (a small molecule inhibitor of TNF-alpha), tacrolimus, modified release (15,19-Epoxy-3H-pyrido(2,1-c)(1,4)oxaazacyclotricosine-1,7,20, 21(4H,23H)-tetrone, 5,6,8,11,12,13,14,15,16,17,18,19,24, 25,26,26a-hexadecahydro-5,19-dihydroxy-3-(2-(4-hydroxy-3-methoxycyclohexyl)-1-methylethenyl)-14,16-dimethoxy-4,10,12,18-tetramethyl-8-(2-propenyl)-, (3S-(3R*(E(1S*, 3S*,4S*)),4S*,5R*,8S*,9E,12R*,14R*,15S*,16R*,18S*, 19S*,26aR*))), NBE-P2 (anti-TNF-alpha protease), glyponectin (a highly active isoform of adiponectin), BN-006 (an orally active, short chain polypeptide down-regulator of TNF-alpha), LCP-Tacro (15,19-Epoxy-3H-pyrido(2,1-c)(1, 4)oxaazacyclotricosine-1,7,20,21 (4H,23H)-tetrone, 5,6,8, 11,12,13,14,15,16,17,18,19,24,25,26,26a-hexadecahydro-5, 19-dihydroxy-3-(2-(4-hydroxy-3-methoxycyclohexyl)-1-methylethenyl)-14,16-dimethoxy-4,10,12,18-tetramethyl-8-(2-propenyl)-, (3S-(3R*(E(1S*,3S*,4S*)),4S*,5R*,8S*,9E, 12R*,14R*,15S*,16R*,18S*,19S*,26aR*))), QR-440 (a naturally derived anti-inflammatory), CYT007-TNFQb (a vaccine designed to elicit anti-TNF-alpha antibodies), ESBA-105 (a fully humanized fragment of the VH/VL domains that inhibits TNF-alpha), CC-10015 (a thalidomide analog), Dom-0100 (an anti-TNFR1 human domain antibody), AN-0128 (3-hydroxypyridine-2-carbonyloxy-bis(3-chloro-4-methylphenyl)borane), PMI-005 (a plant-based TNF-alpha inhibitor), Y-40138 (1-Pyrimidylpiperazine), ARRY-438162 (a MEK inhibitor), MPL-104 (an anti-cytokine compound), TNF-alpha inhibitor, Devgen (an orally administered small molecule TNF-alpha inhibitor), IMD-1041 (an IKappa kinase-β inhibitor), LT-ZMP001 (a tetrapeptide that blocks interaction of TNF with TNFR1), TPL2 inhibitors (small molecule inhibitors of tumor progression loci-2 such as 8-bromo-4-(3-chloro-4-fluorophenylamino)-6-[(1-methyl-1H-imidazol-4-yl)methylamino]quinoline-3-carbonitrile), thiothalidomide and hydroxythalidomide inhibitors of TNF-alpha (Phase 2 Discovery, Inc.), tacrolimus (delivered through a pulmonary drug delivery system) PMI-006c (an anti-inflammatory botanical extract), Pirfenidone (a bioavailable pyridine derivative), PN-0615 (an anti-TNF-alpha human monoclonal antibody), P-979 (Nicholas Piramal), Sphira (an orally active anti-TNF phytopharmaceutical), RPL-228 (a small-molecule synthetic mimetic of the cyclopentenone prostaglandins), THR-090717 (orally available TNF-alpha antagonist), PEG-sTNFR1, CDP-870, sLTr, CDP-571, MAK-195F, SelCIDs, forskolin, rTBP-1, D2E7, OR1384, tenidap, rapamycin, leflunomide, and combinations thereof. Preferably, the TNF-alpha inhibitor is etanercept.

A modulator of the TNF pathway may also be a p38 MAP kinase inhibitor, a PDE4 inhibitor, a TNFR1 inhibitor, or a TNFR2 inhibitor. Such inhibitors may also be TNF-alpha antagonists/inhibitors. In the present invention, p38 MAP kinase inhibitor, a PDE4 inhibitor, a TNFR1 inhibitor, and/or a TNFR2 inhibitor may be selected from the following classes of agents: nucleic acids, polypeptides, polysaccharides, small organic or inorganic molecules, and combinations thereof. Preferably, the TNF-alpha inhibitor may be a fusion protein, including a receptor trap, an antibody, antibody mimetic, domain antibody, targeted aptamer, RNAi, siRNA, shRNA, antisense sequence, small molecule, and polysaccharide.

In the present invention, representative, non-limiting examples of the p38 MAP kinase inhibitor include: semapimod (Decanediamide, N,N'-bis[3,5-bis[1-[(aminoiminomethyl)hydrazono]ethyl]phenyl]-, tetrahydrochloride), SCIO-469 (a small molecule p38-alpha kinase inhibitor), VX-702 (an orally-active p38 MAP kinase inhibitor), PS-540446 (a small molecule p38 kinase inhibitor), LP-7708 (orally active p38 MAP kinase inhibitor), CDP-146 (an orally-active small molecule p38 MAP kinase inhibitor), ARRY-797 (a 1,5-disubstituted-1H-indazole), GSK-681323 (an orally-active p38 MAP kinase inhibitor), R-1628 (Roche), p-38-alpha kinase inhibitors, Amph (an orally-active p38-alpha kinase inhibitor, Amphora), BMS-2 (Bristol-Myers Squibb), SD-282 (a p38-alpha MAP kinase inhibitor), p38 selective inhibitor (Kalypsys), LOC-7590 (an orally-active oncokinase inhibitor), p38 kinase inhibitors (a second generation allosteric p38 MAP kinase inhibitor, Kemia), KC-706 (an orally-active p38 MAP kinase inhibitor that binds to an allosteric (Phe-out) on p38 MAP kinase), TA-5493 (Tanabe Seiyaku), p38 MAPK siRNA (Merck), Org-223119 (Organon), Org-48775 (Organon), 856553 (GlaxoSmithKline), p38 signal inhibitor (Rexahn), p38 MAP Kinase inhibitor (a systemically-delivered p38 MAP kinase inhibitor, Chroma Therapeutics), CHR-3620 (a locally-delivered p38 MAP kinase inhibitor, Chroma Therapeutics), PH-797804 (Pfizer), p38 MAP kinase inhibitor (a benzimidazolone analog p38 MAP kinase inhibitor, Boehringer Ingelheim), Org-217993 (Organon), P38 MAP kinase inhibitor (a 7-amino-napthyridone-based analog, Merck), ARRY-614 (a p38/Tie-2 kinase inhibitor, Array BioPharma), p38-alpha kinase inhibitor (Xcovery), p38 kinase inhibitor (a pyrazolo-pyrimidine analog, Bristol-Myers Squibb), SD-169 (an indole-5-carboxamide p38-alpha MAP kinase-selective inhibitor), p38 MAP kinase inhibitor (a naphthyridinone analog p38 MAP kinase inhibitor, Merck), and combinations thereof.

In the present invention, representative, non-limiting examples of the PDE4 inhibitor include: ibudilast (1-Propanone, 2-methyl-1-[2-(1-methylethyl)pyrazolo[1,5-a]pyridin-3-yl]), tetomilast (a non-peptidic, thiazole derivative, such as 2-Pyridinecarboxylic acid, 6-[2-(3,4-diethoxyphenyl)-4-thiazolyl]), cilomilast (an orally-active PDE4 inhibitor having the structure Cis-4-cyano-4-[3-(cyclopentyloxy)-4-methoxyphenyl]cyclohexane-1-carboxylic acid), roflumilast (Benzamide, 3-(cyclopropylmethoxy)-N-(3,5-dichloro-4-pyridinyl)-4-(difluoromethoxy)), IC-486051 (a PDE4 inhibitor that targets PDE4A, PDE4B, PDE4C and PDE4D isoforms, Eli Lilly), IPL-455903 (an orally-active PDE4 inhibitor), MEM-1414 (Memory Pharmaceuticals), etazolate (an orally-available PDE4B inhibitor having the structure 1H-Pyrazolo[3,4-b]pyridine-5-carboxylic acid, 1-ethyl-4-[(1-methylethylidene)hydrazino]-, ethyl ester), MN-001 (an orally-active PDE4 inhibitor, Kyorin), PLX-369 (a selective PDE4B inhibitor), ND-1251 (an orally-active PDE4 inhibitor), ND-1510 (Evotec), apremilast ((CC-10004), an orally-active SelCID having the structure Acetamide, N-[2-[(1S)-1-(3-ethoxy-4-methoxyphenyl)-2-(methylsulfonyl)ethyl]-2,3-dihydro-1,3-dioxo-1H-isoindol-4-yl]), CC-11050 ((CC-5048), an orally active SelCID, Celgene), PDE IV inhibitor (a PDE4D inhibitor, deCODE), PDE IV inhibitors (Memory Pharmaceuticals), MEM-1917 (Memory Pharmaceuticals), oglemilast (an orally-active PDE4 inhibitor, Glenmark)), ELB-353 (an orally-active PDE4 inhibitor, Elbion), PDE IV inhibitor (Crystal Genomics), TPI-1100 (an inhaled RNAi or antisense oligonucleotide, Topigen), AVE-8112 (Sanofi-Aventis), CC-10015 (a thalidomide analog, Celgene), LAS-37779 (a topical PDE4 inhibitor, Almirall-Prodesfarma), CHF-5480 (a PDE4 inhibitor administered by inhalation, Chiesi), AV-411 (an orally-available formulation of ibudilast, Avigen), PDE IV inhibitor (Elbion), PDE IV inhibitor (Tanabe Seiyaku), 256066 (a PDE4 inhibitor administered by inhalation), PDE IV inhibitor (Aurigene Discovery Technologies), YM-393059 ((Å±)-N-(4,6-dimethylpyrimidin-2-yl)-4-[2-(-(4-methoxy-3-methylphenyl)-5-(4-methylpiperazin-1-yl)-4,5,6,7-tetrahydro-1H-indol-1-yl]benzenesulfonamide difumarate), AN-2728 (a topical PDE4 inhibitor), PDE IVB inhibitor (deCODE), GRC-4039 (Glenmark), DE-103 (Santen), RPL-554 (Verona Pharma), PDE IV Inhibitor (a PDE4 inhibitor administered by inhalation, Almirall-Prodesfarma), PDE IV inhibitor (VIA Pharmaceuticals), IPL-42 (Inflazyme), and combinations thereof.

In the present invention, non-limiting examples of the TNFR1 and TNFR2 receptor inhibitors include: pirfenidone (2(1H)-Pyridinone, 5-methyl-1-phenyl-), GT-111 (an iv gene therapy containing a smart chimeric gene, Vascular Biogenics), CYT-6091 (aurimmune colloidal gold nanoparticle that is a PEGylated formulation of TNF-alpha), TNF-alpha kinoid (a kinoid vaccine which induces the synthesis of potent human polyclonal antibodies against TNF-alpha), apremilast (Acetamide, N-[2-[(1S)-1-(3-ethoxy-4-methoxyphenyl)-2-(methylsulfonyl)ethyl]-2,3-dihydro-1,3-dioxo-1H-isoindol-4-yl]-), C-11050 (an orally-active SelCID (selective cytokine inhibitory drug) that inhibits TNF-alpha and phosphodiesterase IV), YSIL (a TNF-alpha antagonist), Dom-0100 (an anti-TNFR1 human domain antibody (dAb)), PMI-005 (a plant-based TNF-alpha inhibitor), BreMel/TNF-alpha (an unglycosylated, low molecular weight recombinant fusion protein consisting of a single chain antibody fragment (scFv) genetically fused to human TNF-alpha), Y-40138 (a TNF-alpha inhibitor), ARRY-438162 (Array BioPharma), LT-ZMP001 (a tetrapeptide that blocks the interaction of TNF with TNFR1), pirfenidone analog (InterMune), RPL-228 (a small-molecule synthetic mimetic of the cyclopentenone prostaglandins and topical TNF-alpha inhibitor), and combinations thereof.

As noted above, a modulator of the TNF pathway may act upstream or downstream of TNF-alpha. For example, it is well established that inhibition of p38 MAP kinase correlates with a decrease in, e.g., cellular activity of TNF-alpha. See, e.g., Peifer et al., New approaches to the treatment of inflammatory disorders small molecule inhibitors of p38 MAP kinase, Curr Top Med Chem., 6(2):113-49 (2006), Saklatvala, The p38 MAP kinase pathway as a therapeutic target in inflammatory disease, Curr Opin Pharmacol, 4(4):372-7 (2004), and Miwatashi et al., Novel inhibitor of p38 MAP kinase as an anti-TNF-alpha drug: discovery of N-[4-[2-ethyl-4-(3-methylphenyl)-1,3-thiazol-5-yl]-2-pyridyl]benzamide (TAK-715) as a potent and orally active anti-rheumatoid arthritis agent, J Med Chem. 48(19):5966-79 (2005). Indeed, it is known that p38 MAP kinase regulates the biosynthesis of TNF-alpha at both the transcriptional and translational levels (See, e.g., Lee et al., A protein kinase involved in the regulation of inflammatory cytokine biosynthesis, Nature 372(6508):739-746 (1994) and Kumar et al., p38 MAP kinases: Key signaling molecules as therapeutic targets for inflammatory diseases, Nat Rev Drug Discov, 2(9):717-726 (2003)) and a number of p38 MAP kinase inhibitors have been characterized in vitro and advanced into clinical trials (see, e.g., Wagner and Laufer, Small Molecular Anti-Cytokine Agents, Medicinal Research Reviews, 26(1):1-62 (2006)).

It is also well established that inhibition of PDE4 correlates with a decrease in, e.g., production of TNF-alpha, as well as suppression of TNF-alpha mRNA transcription and thus synthesis. See, e.g., Marx et al., Modulation of TNF and GM-CSF release from dispersed human nasal polyp cells and human whole blood by inhibitors of different PDE isoenzymes and glucocorticoids, Pulm Pharmacol Ther, 15(1):7-15 (2002) and Morjaria et al., Impairment of TNF-alpha production and action by imidazo[1,2-alpha]quinoxalines, a derivative family which displays potential anti-inflammatory properties, Int J Immunopathol Pharmacol, 19(3):525-38 (2006). For example, production of TNF-alpha has repeatedly been shown to be potently abrogated in the presence of PDE4 inhibitors in vitro (Semmler et al., The specific type IV phosphodiesterase inhibitor rolipram suppresses tumor necrosis factor-α production by human mononuclear calls, Int J Immunopathol Pharmacol, 15:409-413 (1993); Schade & Schudt, The specific type III and type IV phosphodiesterase inhibitor zardaverine suppressed tumor necrosis or by macrophages, Eur J Pharmacol 230:9-14 (1993); Schudt et al., Effect of phosphodiesterase (PDE) inhibitors on activation of human macrophages and lymphocytes, Eur Res J, 6(Suppl. 17):367S (1993); Schudt et al., PDE isoenzymes as targets for anti-asthmatic drugs, Eur Res J, 8:1179-1183 (1995); Prabhakar et al., Characterization of cAMP-dependent inhibition of LPS-induced TNF alpha production by rolipram, a specific phosphodiesterase IV (PDE IV) inhibitor, Int J Immunopharmacol, 16:805-816 (1994); Seldon et al., Suppression of lipopolysaccharide-induced tumor necrosis factor-α generation from human peripheral blood monocytes by inhibitors of phosphodiesterase 4: interaction with stimulants of adenylyl cyclase, Mol Pharmacol, 48:747-757 (1995)) and in vivo (Fischer et al., Protection by phosphodiesterase inhibitors against endotoxin-induced liver injury in galactosamine-sensitized mice, Biochem Pharmacol, 45:2399-2404 (1993); Sommer et al., The antidepressant rolipram suppresses cytokine production and prevents autoimmune encephalomyelitis, Nature Med, 1, 244-248 (1995); Genain et al., Prevention of autoimmune demyelination in non-human primates by cAMP-specific phosphodiesterase inhibitor, Natl Acad Sci U.S.A., 92: 3601-3605 (1995); Gantner et al., Protection from T cell-mediated murine liver failure by phosphodiesterase inhibitors, J Pharmacol Exp Ther, 280: 53-60 (1997)). Thus, in view of the link disclosed herein between TNF-alpha inhibition, FIP2 regulation, and PC2 localization, expression and function, the present invention has established a basis that modulators of the TNF pathway that are both upstream and downstream of TNF-alpha are likely to regulate PC2 localization, function, and/or expression and may be viable options to treat, e.g., PC2-related disorders, such as polycystic diseases particularly PKD.

A non-limiting example of a modulator that acts downstream of TNF-alpha is an agent that acts as a FIP2 inhibitor as previously defined.

g. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, shRNA, siRNA, Piwi-interacting RNA, pri-miRNA, pre-miRNA, miRNA, or anti-miRNA, as described, e.g., in U.S. patent application Ser. No. 11/429,720, Ser. No. 11/384,049, Ser. No. 11/418,870, and Ser. No. 11/429,720 and Published International Application Nos. WO 2005/116250 and WO 2006/126040.

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

h. Peptide, Polypeptide, Protein

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No. 20070065447.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64(8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253(5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307(1):198-205. Additional discussion of related principles, methods, etc., that may be applicable in the context of this invention are provided in, e.g., Fassina, Immunomethods. October 1994; 5(2):121-9.

As used herein, "peptide" includes targeted proteases, which are capable of, e.g., substrate-targeted inhibition of post-translational modification such as disclosed in, e.g., U.S. Patent Application Publication No. 20060275823.

In the present invention, "peptide" further includes anticalins. Anticalins can be screened for specific binding to a modulator of the TNF pathway such as TNF-alpha, fragments of a modulator of the TNF pathway such as TNF-alpha, or variants of a modulator of the TNF pathway such as TNF-alpha. Anticalins are ligand-binding proteins that have been constructed based on a lipocalin scaffold (Weiss, G. A. and H. B. Lowman (2000) Chem. Biol. 7:R177-R184; Skerra, A. (2001) J. Biotechnol. 74:257-275). The protein architecture of lipocalins can include a beta-barrel having eight antiparallel beta-strands, which supports four loops at its open end. These loops form the natural ligand-binding site of the lipocalins, a site which can be re-engineered in vitro by amino acid substitutions to impart novel binding specificities. The amino acid substitutions can be made using methods known in the art, and can include conservative substitutions (e.g., substitutions that do not alter binding specificity) or substitutions that modestly, moderately, or significantly alter binding specificity.

i. Small Organic or Inorganic Molecules

The phrase "small organic or inorganic molecule" includes any chemical or other moiety, other than polypeptides and nucleic acids, that can act to affect biological processes. Small molecules can include any number of therapeutic agents presently known and used, or can be synthesized in a library of such molecules for the purpose of screening for biological function(s). Small molecules are distinguished from macromolecules by size. The small molecules of this invention usually have a molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds. Methods for preparing peptidomimetics are described below. Collections of small molecules, and small molecules identified according to the invention are characterized by techniques such as accelerator mass spectrometry (AMS; see Turteltaub et al., Curr Pharm Des 2000 6:991-1007, Bioanalytical applications of accelerator mass spectrometry for pharmaceutical research; and Enjalbal et al., Mass Spectrom Rev 2000 19:139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids. Examples of some peptidomimetics by the broader definition (e.g., where part of a polypeptide is replaced by a structure lacking peptide bonds) are described below. Whether completely or partially non-peptide in character, peptidomimetics according to this invention may provide a spatial arrangement of reactive chemical moieties that closely resembles the three-dimensional arrangement of active groups in a polypeptide. As a result of this similar active-site geometry, the peptidomimetic may exhibit biological effects that are similar to the biological activity of a polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that may be reduced with peptidomimetics.

Polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure, shape or reactivity. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98.

j. Treating/Ameliorating

"Treatment" or "treating," as used herein means preventing, suppressing, repressing, or completely eliminating a disease. Preventing a disease involves administering a composition of the present invention to an animal prior to onset of the disease. Suppressing the disease involves administering a composition of the present invention to an animal after induction of a disease but before its clinical appearance. Repressing the disease involves administering a composition of the present invention to an animal after clinical appearance of the disease. "Ameliorating" an effect of a disease means that at least one symptom of the disease is eliminated or decreased.

2. Polycystic Disorders

A method is provided herein for treating or ameliorating an effect of a polycystic disease. The method may comprise administering to a patient in need thereof an amount of a modulator of a TNF pathway, such as the TNF-alpha pathway, that is sufficient to treat or ameliorate an effect of a polycystic disease.

a. FIP2 Role in PC1/PC2 Transmembrane Complexes

While not being bound by theory, FIP2, which is in the TNF pathway, including the TNF-alpha pathway, may be an adaptor protein that is involved in vesicular trafficking. FIP2 may recruit various membrane traffic factors by targeting complexes to cellular membranes. FIP2 may disrupt Polycystin-2 (PC2) localization to the cell membranes by sequestering PC2 in the perinuclear regions. Increasing FIP2 expression may further sequester PC2 from PC1 in the perinuclear regions. FIP2's disruption of PC2 localization may, in turn, prevent PC2 from forming transmembrane complexes with PC1. Disruption of PC1/PC2 transmembrane complexes by FIP2 may lead to cystogenesis, and ultimately a polycystic disease, due to decreased levels of cell differentiation, increased rates of cell proliferation, apoptosis, and transepithelial fluid secretion. Increased FIP2 expression may also promote cyst formation in humans with autosomal dominant or autosomal recessive mutations of Pkd1 or Pkd2.

FIP2 may be downregulated in differentiating cells, thereby allowing PC1 and PC2 to form transmembrane complexes. Without FIP2 disruption of PC2, the transmembrane complex may be formed through an interaction between PC1 and PC2's cytoplasmic domains and may be localized to the primary cilia at the apical surface of renal epithelial cells. Cilium may be an organelle that extends the basal body and contains organized arrays of microtubules and associated proteins. PC1 and PC2 transmembrane complexes may also mediate calcium signaling and interact with structural proteins that regulate epithelial cell proliferation and morphogenesis. Thus, proper FIP2 regulation may be critical in maintaining proper rates of cell division and differentiation in order to prevent cystogenesis of renal epithelial cells and ultimately on-set of a polycystic disease.

b. TNF-Alpha's Role in FIP2 Expression Through a Double Negative Feedback Loop

Figure 4:
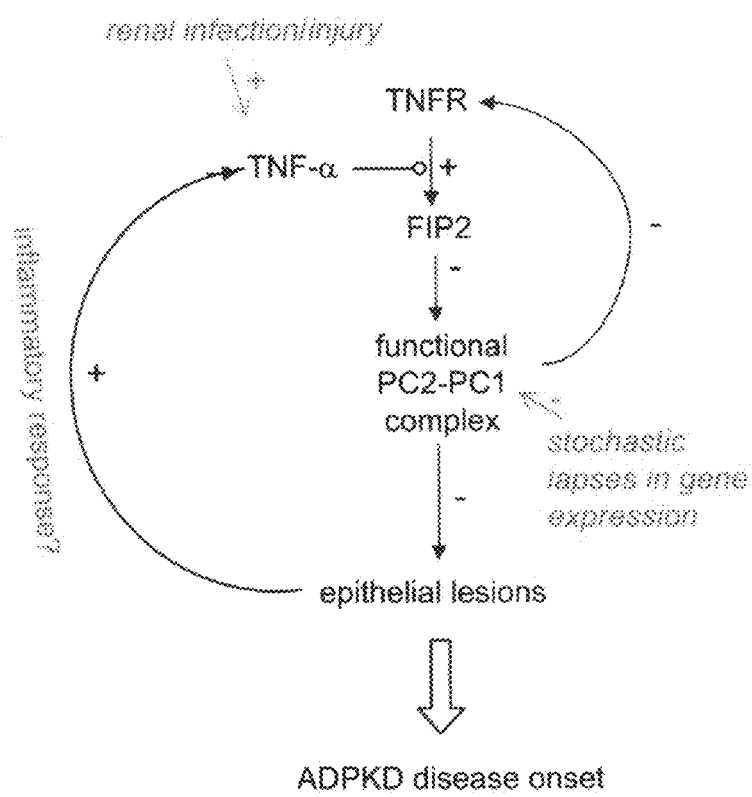
FIG. 4 shows a functional network connecting TNF-alpha signaling, FIP2 expression, PC2 disruption, and cystogenesis/disease onset.

While not being bound by theory, TNF-alpha may affect the normal trafficking of PC2 through induction of FIP2 expression through a double negative feedback loop process, which may contribute to the transition from normal tubule development to renal cystic, i.e., polycystic, disease. As shown in FIG. 4, an acute or chronic increase in TNF-alpha levels may lead to increased TNF-alpha receptor signaling, which, in turn, induces FIP2 expression, which, in turn, disrupts PC1/PC2 transmembrane complexes, which, in turn, leads to cystogenesis, including on-set of a polycystic disease, as described above. The acute or chronic levels of TNF-alpha may activate this feedback loop and lead to a sudden and sustained decline of functional polycystins (PC2/PC1). Cystogenesis may further increase levels of TNF-alpha thereby perpetuating TNF-alpha signaling and induction of FIP2 expression. Although normal individuals may have polycystin function above a critical threshold, the ADPKD heterozygous genetic background may be particularly sensitive to TNF-alpha signaling due to already reduced Pkd1 or Pkd2 gene expression. A stochastic trigger of this epigenetic switch may result from fluctuation in gene expression, which occurs at higher amplitudes and can have a greater impact with reduced gene copy number as in the heterozygous situation.

c. Polycystic Disease

A polycystic disease may, therefore, be treated by decreasing the activity of, e.g., TNF-alpha, FIP2, or an agent that directly or indirectly inhibits TNF-alpha and/or FIP2 in the cell. Thus, the present invention, includes any agent in the TNF pathway, particularly the TNF-alpha pathway, that modulates, preferably reducing or inhibiting, TNF-alpha and/or FIP2 expression, which leads to alleviation of a polycystic or other disease phenotype including restoration of PC2 function, expression, and/or localization in the plasma membrane and/or primary cilia. The FIP2-related disorder may be polycystic kidney disease (PKD), which, in turn, may include autosomal dominant polycystic kidney disease (ADPKD) or autosomal recessive polycystic kidney disease (ARPKD). The polycystic disease may also be polycystic liver disease (PLD), polycystic ovary syndrome (PCOS), pancreatic cysts, or cancer.

d. TNF-Pathway Modulators

A polycystic disease may be treated or an effect of the disease may be ameliorated by administering to a patient, e.g., an animal such as a mammal, preferably a human, an amount of a modulator of the TNF pathway, preferably, the TNF-alpha pathway, which amount is sufficient to treat or ameliorate an effect of the polycystic disease. Such a modulator may act directly or indirectly on TNF-alpha and/or FIP2 and lead to a decrease in TNF-alpha and/or FIP2 expression, function, and/or activity and ultimately to increased PC2 localization in the plasma membrane and/or cilia of a PC2 expressing cell and/or increased PC2 expression and/or function.

The TNF pathway modulator may be administered to a patient in need thereof at an amount which is sufficient to treat or ameliorate an effect of a polycystic disease. Preferably, the amount is a therapeutically effective amount. The TNF pathway modulator may decrease FIP2 gene expression. The TNF pathway modulator may reduce the level of FIP2 signaling to allow interaction of PC1 and PC2. The TNF-alpha pathway modulator may reduce the level of FIP2 expression to allow PC1 and PC2 to form transmembrane complexes, which control the cell cycle, prevent cell proliferation, and promote cell differentiation. The TNF pathway modulator may restore membrane localization of PC2 due to modulation of FIP2 expression.

The TNF pathway modulator may be a nucleic acid, polypeptide, polysaccharide, small organic or inorganic molecule, or combinations thereof. In one embodiment, the TNF pathway modulator may be a polypeptide, polypeptide fragment, or derivative thereof. The polypeptide may be an anti-FIP2 antibody or fragment thereof that binds FIP2 and inhibits its interaction with PC2. The TNF pathway modulator may be a nucleic acid. The nucleic acid may be a siRNA that is complementary to a FIP2 encoding mRNA. The TNF pathway modulator may be a TNF-alpha inhibitor. The TNF-alpha inhibitor may prevent TNF-alpha signaling. A decrease or abortion of TNF-alpha signaling may reduce or sequester FIP2 expression. The TNF-alpha inhibitor may thereby prevent FIP2 expression from sequestering PC2, thus modulating polycystin function to control the cell cycle, prevent cell proliferation, and promote cell differentiation. Murine models may be used to determine a dosage and administration of TNF pathway modulators for treatment of polycystic diseases, including PKD related disorders in humans. A TNF-alpha inhibitor may be used to treat or ameliorate the effects of PKD by administering a TNF-alpha inhibitor to a patient in need thereof at an amount, preferably a therapeutically effective amount of the TNF-alpha inhibitor to treat or ameliorate an effect of PKD.

(1) Etanercept

The TNF-alpha inhibitor may be etanercept, which is commercially known as Enbrel®. As noted above, etanercept may be a recombinant fusion protein consisting of two soluble TNF receptors joined by the Fc fragment of a human IgG1 molecule. Etanercept is a Food and Drug Administration-approved drug that may comprise the extracellular ligand-binding portion of the human 75 kDa (p75) TNF receptor 2, which binds and inactivates circulating TNF-alpha with well-characterized pharmacodynamics. Etanercept and its common methods of administration and delivery are disclosed, e.g., in WO-09103553, WO-09406476, U.S. Pat. Nos. 5,605,690, 6,015,557, 6,358,508, 6,379,666, 6,419,934, 6,428,787, 6,423,321, 6,419,944, 6,455,040, 6,503,184, 6,537,549, 6,541,224, and 6,689,607.

(2) Other Modulators of the TNF Pathway

Exemplary modulators of the TNF pathway are disclosed above. Preferred modulators of the TNF pathway include FIP2 inhibitors, p38 MAP kinase inhibitors, PDE4 inhibitors, TNFR1 inhibitors, and TNFR2 inhibitors. Methods of making modulators of the TNF pathway are within the skill of the art. Exemplary methods of making and using certain of the modulators of the TNF pathway are disclosed, e.g., in U.S. Pat. Nos. 5,395,760, 5,605,690, 5,945,397, 5,981,701, RE36, 755, 6,271,346; 6,291,646, and, 7,226,593.

(3) Formulation

A modulator of a TNF pathway according to the present invention may be administered to treat a polycystic or other related disease in a number of different formulations. A soluble modulator of a TNF pathway may be administered in the form of a composition comprising purified protein in conjunction with physiologically acceptable carriers, excipients or diluents. Such carriers may be nontoxic to recipients at the dosages and concentrations employed. The preparation of such compositions may entail combining the modulator of a TNF pathway with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin may be appropriate diluents. The modulator of a TNF pathway may be formulated as a lyophilizate using appropriate excipient solutions (e.g., sucrose) as diluents. Appropriate dosages of the modulator of a TNF pathway may be determined in trials. In accordance with appropriate industry standards, preservatives may also be added, such as benzyl alcohol.

The modulator of a TNF pathway may be formulated as a tablet or lozenge in a conventional manner. For example, tablet or lozenge capsules may contain conventional excipients such as a binding compound, filler, lubricant, disintegrant or wetting compound. The binding compound may be syrup, accacia, gelatin, sorbitol, tragacanth, mucilage of starch or polyvinylpyrrolidone. The filler may be lactose, sugar, microcrystalline cellulose, maizestarch, calcium phosphate, or sorbitol. The lubricant may be magnesium stearate, stearic acid, talc, polyethylene glycol, or silica. The disintegrant may be potato starch or sodium starch glycollate. The wetting compound may be sodium lauryl sulfate. Tablets may be coated according to methods well known in the art.

The modulator of a TNF pathway may also be a liquid formulation which may be an aqueous or oily suspension, solution, emulsion, syrup, or elixir. The modulator of a TNF pathway may also be formulated as a dry product for constitution with water or other suitable vehicle before use. Such liquid preparations may contain an additive such as a suspending compound, emulsifying compound, nonaqueous vehicle or preservative. The suspending compound may be a sorbitol syrup, methyl cellulose, glucose/sugar syrup, gelatin, hydroxyethylcellulose, carboxymethyl cellulose, aluminum stearate gel, or a hydrogenated edible fat. The emulsifying compound may be lecithin, sorbitan monooleate, or acacia. The nonaqueous vehicle may be an edible oil, almond oil, fractionated coconut oil, oily ester, propylene glycol, or ethyl alcohol. The preservative may be methyl or propyl p-hydroxybenzoate, or sorbic acid.

The modulator of a TNF pathway may also be formulated as a suppository, which may contain suppository bases which may be cocoa butter or glycerides. The modulator of a TNF pathway may also be formulated for inhalation, which may be in a form such as a solution, suspension, or emulsion that may be administered as a dry powder or in the form of an aerosol using a propellant, such as dichlorodifluoromethane or trichlorofluoromethane. The modulator of a TNF pathway may also be a transdermal formulation comprising an aqueous or nonaqueous vehicle which may be a cream, ointment, lotion, paste, medicated plaster, patch, or membrane.

The modulator of a TNF pathway may also be formulated for parenteral administration, which may be by injection or continuous infusion. Formulations for injection may be in the form of a suspension, solution, or emulsion in oily or aqueous vehicles, and may contain a formulation compound such as a suspending, stabilizing, or dispersing compound. The modulator of a TNF pathway may also be provided in a powder form for reconstitution with a suitable vehicle such as sterile, pyrogen-free water.

The modulator of a TNF pathway may also be formulated as a depot preparation, which may be administered by implantation or by intramuscular injection. The modulator of a TNF pathway may be formulated with a suitable polymeric or hydrophobic material (as an emulsion in an acceptable oil, for example), ion exchange resin, or as a sparingly soluble derivative (as a sparingly soluble salt, for example).

The modulator of a TNF pathway may also be formulated as a liposome preparation. The liposome preparation may comprise a liposome which penetrates the cells of interest or the stratum corneum, and fuses with the cell membrane, resulting in delivery of the contents of the liposome into the cell. For example, the liposome may be as disclosed in U.S. Pat. No. 5,077,211 of Yarosh, U.S. Pat. No. 4,621,023 of Redziniak et al. or U.S. Pat. No. 4,508,703 of Redziniak et al. Other suitable formulations may employ niosomes. Niosomes are lipid vesicles similar to liposomes, with membranes consisting largely of non-ionic lipids, some forms of which are effective for transporting compounds across the stratum corneum.

(4) Administration of a Modulator of a TNF Pathway

A modulator of a TNF pathway may be administered orally, parenterally, sublingually, transdermally, rectally, transmucosally, topically, via inhalation, via buccal administration, or combinations thereof. Parenteral administration may be intravenous, intraarterial, intraperitoneal, subcutaneous, intramuscular, intrathecal, or intraarticular. The modulator of a TNF pathway may also be administered in the form of an implant, which allows slow release of the agent as well as a slow controlled i.v. infusion. For treating mammals according to the methods of the present invention, subcutaneous injection may be used because many modulators of a TNF pathway are destroyed by the digestive process or otherwise ineffective if ingested.

(5) Dosage of a Modulator of a TNF Pathway

An amount sufficient to treat or ameliorate an effect of a polycystic or other related disease, such as a therapeutically effective amount of a modulator of a TNF pathway, may vary with the nature of the condition being treated, the length of time that activity is desired, and the age and the condition of the patient, and ultimately may be determined by the attendant physician. The amount or dose of a modulator of a TNF pathway that may be administered to a patient may also vary depending on a variety of factors known in the art (e.g., species, sex, age, weight, condition of the patient, desired response, nature of the condition, metabolism, severity of disease, side-effects). In general, however, doses employed for adult human treatment typically may be in the range of 0.0001 mg/kg/day to 0.0010 mg/kg/day, 0.0010 mg/kg/day to 0.010 mg/kg/day, 0.010 mg/kg/day to 0.10 mg/kg/day, 0.10 mg/kg/day to 1.0 mg/kg/day, 1.00 mg/kg/day to about 200 mg/kg/day. The dosage may be 2-10 mg/kg/day, 10-50 mg/kg/day, or 50-100 mg/kg/day. The dose may be about 1 mg/kg/day to about 100 mg/kg/day. In a preferred embodiment, the dose administered to a human being may be about 25 mg, twice weekly, or about 50 mg, once weekly (e.g. subcutaneous injection). The desired dose may be conveniently administered in a single dose, or as multiple doses administered at appropriate intervals, for example as two, three, four or more subdoses per day. Multiple doses often are desired, or required.

A number of factors may lead to the modulator of a TNF pathway being administered at a wide range of dosages. When given in combination with other therapeutics, the dosage of the modulator of a TNF pathway of the present invention may be given at a relatively lower dosage. In addition, the use of a targeting substituent may allow the necessary dosage to be relatively low. The modulator of a TNF pathway may be administered at a relatively high dosage, which may be due to a factor such as low toxicity, high clearance, or low rates of processing. As a result, the dosage of the modulator of a TNF pathway may be from about 1 ng/kg to about 1000 mg/kg. The dosage of the modulator of a TNF pathway may be at any about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

3. Murine Model for Polycystic Disease

The disclosed method of treating or ameliorating the effect of a polycystic disease with a modulator of a TNF pathway may be based upon murine models. For example, those skilled in the art study human PKD using a PKD loss of function mutant mouse because various strains of mutant mice exhibit disease symptoms that parallel both ADPKD and ARPKD. See "Polycystic Kidney Disease," retrieved from the National Institute of Diabetes and Digestive and Kidney Diseases website. Mouse models for polycystic diseases may be possible, in part, because the molecular pathways underlying the pathology of PKD cyst formation are shared by both mice and humans. Polycystin-1 and polycystin-2, which are products of the PKD-1 and PKD-2 genes, respectively, may exhibit the same kidney cell localization in mice and humans (Cano et al., Development, 2004; 131: 3457-67).

Studies using PKD mouse mutants aim at understanding the genetic and nongenetic mechanisms involved in cyst formation, and at discovering candidate compounds that inhibit cyst formation in PKD mutants. As disclosed above, the inventors have discovered that a modulator of a TNF pathway, such as for example, a TNF-alpha inhibitor, may be used to inhibit cyst formation associated with PKD. In addition, much of what is known in the field about the role of TNF-alpha signaling comes from studies in rodents, especially mice and rats. Rodents that overexpress TNF-alpha may develop symptoms much like rheumatoid arthritis, a human disease associated with excess TNF-alpha and inflammatory signaling (Palladino et al. Nature Drug Discovery, 2003; 2:736-46). Hence, studies of TNF-alpha in the mouse are thought by those skilled in the art to be directly relevant to TNF-alpha signaling in humans. Many known TNF-alpha inhibitors used to treat human diseases, such as rheumatoid arthritis, were tested and confirmed to be effective in mice before being tested in humans.

4. Methods for Identifying Candidate Compounds

Another embodiment of the invention is a method for identifying a candidate compound that may be effective to treat or ameliorate an effect of a polycystic disease or to increase polycystin-2 (PC2) function or decrease Rab11-Family of Interacting Protein-2 (FIP2) function. This method includes (a) contacting a test cell that expresses PC-2 with an amount of a TNF-alpha pathway modulator, which is effective to modulate FIP2 expression in the test cell and/or to disrupt PC2 localization or function at a plasma membrane or a primary cilia of the test cell, (b) further contacting the test cell from step (a) with a candidate compound, and (c) determining whether the candidate compound increases PC2 localization to the plasma membrane of the test cell, the primary cilia of the test cell, or both or increases PC2 function or decreases FIP2 expression in the test cell compared to a control cell treated in an identical fashion except that it was not contacted with the candidate compound, wherein a candidate compound that increases PC2 localization to the plasma membrane of the test cell, the primary cilia of the test cell, or both or increases PC2 function or decreases FIP2 expression in the test cell relative to the control cell is indicative that the candidate compound may be effective to treat or ameliorate the effects of a polycystic disease or to increase PC2 function or decrease FIP2 expression.

In this method, the candidate compound may be any molecule capable of modulating a gene or gene product in the TNF-alpha pathway, which results in an increase in PC2 localization to the plasma membrane of the test cell, the cilia, particularly the primary cilia, of the test cell, or both, or increases PC2 function, or modulates, preferably decreases, FIP2 expression or function in the test cell line. In the present invention, the candidate compound may be a biological or non-biological agent. Preferably, the candidate compound is a nucleic acid, polypeptide, polysaccharide, or small organic or inorganic molecule as previously defined.

In this method, non-limiting examples of TNF-alpha pathway members that may be modulated include necrosis factor (TNF)-alpha, TNF-alpha receptor, tissue necrosis factor receptor-1 (TNFR1), tissue necrosis factor receptor-2 (TNFR2), Fas-associated death domain protein (FADD), Rab11-Family of Interacting Protein-2 (FIP2), TNF-receptor-associated death domain protein (TRADD), receptor-interacting protein-1 (RIP-1), TNF receptor-associated factors (TRAFs), phosphodiesterase IV (PDE4), p38 mitogen activated protein (MAP) kinase, fibrocystin, or a TNF-alpha-associated polypeptide. Preferably, the TNF-alpha pathway member that may be modulated is selected from a TNF-alpha inhibitor, a p38 MAP kinase inhibitor, a PDE4 inhibitor, a FIP2 inhibitor, a TNFR1 inhibitor, or a TNFR2 inhibitor.

The test cell line must express PC2. Non-limiting examples of PC2-expressing cell lines include epithelial cells, endothelial cells, vascular smooth muscle cells, skeletal muscle, osteoblasts/osteocytes, B-lymphoblastoid cells, astrocytes, and neurons. See, e.g., Ibraghimov-Beskrovnanya et al, Polycystin: in vitro synthesis, in vivo tissue expression, and subcellular localization identifies a large membrane-associated protein. Proc Natl Acad Sci USA. 1997 Jun. 10; 94(12):6397-402; Chauvet V et al, Expression of PKD1 and PKD2 transcripts and proteins in human embryo and during normal kidney development. Am J Pathol. 2002 March; 160(3):973-83; Torres V E et al, Vascular expression of polycystin-2. J Am Soc Nephrol. 2001 January; 12(1):1-9; Markowitz G S et al, Polycystin-2 expression is developmentally regulated. Am J Physiol. 1999 July; 277(1 Pt 2):F17-25; Aquiari G et al, Deficiency of polycystin-2 reduces Ca2+ channel activity and cell proliferation in ADPKD lymphoblastoid cells. FASEB J. 2004 May; 18(7):884-6; Stokely M E et al, Polycystin-1 can interact with homer 1/Vesl-1 in postnatal hippocampal neurons. J Neurosci Res. 2006 December; 84(8):1727-37; and Xiao Z et al, Cilia-like structures and polycystin-1 in osteoblasts/osteocytes and associated abnormalities in skeletogenesis and Runx2 expression. J Biol Chem. 2006 Oct. 13; 281(41):30884-95. Preferably, the test cell is obtained from a normal or a PKD-affected organism. The organism may be a mammal, such as for example, a rodent or a human. It is also preferred that the test cell be a kidney cell, such as for example an inner medullary collecting duct (IMCD) cell line or an ADPKD2 cell line. As used herein, the cell may be a primary or immortalized cell line or from an organ culture.

Preferably, the method is carried out as a high throughput screen. Various methods well known in the art may be used to determine whether the candidate compound increases PC2 localization to the plasma membrane of the test cell, the cilia, particularly the primary cilia, of the test cell, or both, or increases PC2 function, or modulates, preferably decreases, FIP2 expression in the test cell line. Certain of these methods are disclosed in more detail in the Examples. Other methods for the determinations called for include measuring calcium flux, using a FIP2 reporter gene, carrying out high throughput RT PCR, immunolocalization, immunohistochemistry, immunoassay and/or PC2 fusion assays. See, e.g., Held et al., U.S. Patent Application Publication No. 20030148264 and Burger et al., Drug Screening Using Cell Lines: Cell Supply, High-Throughput and High-Content Assays, pp. 127-151 in Drug Testing In Vitro: Breakthroughs and Trends in Cell Culture Technology, Marx and Sandig eds. Wiley-VCH 2007.

Candidate compounds that increase PC2 localization to the plasma membrane of the test cell, the cilia, particularly the primary cilia, of the test cell, or both, or increase PC2 function, or modulate, preferably decrease, FIP2 expression in the test cell line may be useful for treating a patient with a polycystic disease as defined previously or for treating a patient with an elevated level of TNF-alpha, FIP2, or both. Preferably, the candidate compounds may be useful to treat a polycystic disease selected from polycystic kidney disease (PKD), polycystic liver disease (PLD), polycystic ovary syndrome (PCOS), pancreatic cysts, and combinations thereof. Preferably, such candidate compounds will be useful to treat autosomal dominant polycystic disease (ADPKD) or autosomal recessive polycystic kidney disease (ADPKD).

In another embodiment, the invention is a method for identifying a patient having, or who is at risk for developing, a polycystic disease. This method includes determining whether the patient has an elevated level of TNF-alpha, FIP2, or both, compared to control levels of TNF-alpha, FIP2, or both in a patient population that does not have the polycystic disease, wherein a patient that has an elevated level of TNF-alpha, FIP2, or both to the control has, or is at risk of developing, a polycystic disease. In this embodiment, the step of determining whether a patient has an elevated level of TNF-alpha, FIP2 or both includes taking an appropriate sample of a body tissue or fluid from the patient, carrying out an assay to determine the TNF-alpha and/or FIP2 levels and comparing the result to a so-called normal or control value, which is obtained from a patient population that does not have the disease. Assays for determining TNF-alpha and FIP2 are disclosed in the Examples and additional assays are known in the art.

In another embodiment, the invention is a method for identifying a patient who may benefit from treatment with a TNF-alpha inhibitor. This method includes determining whether a patient has an elevated level of TNF-alpha, FIP2, or both, compared to control levels of TNF-alpha, FIP2, or both in a patient population that does not have the polycystic disease, wherein a patient that has an elevated level of TNF-alpha, FIP2, or both compared to the control may benefit from treatment with a TNF-alpha inhibitor. The same methods and procedures for determining TNF-alpha and FIP2 disclosed in the application may be used in this embodiment as well.

The invention now being generally described, it will be more readily understood by reference to the following examples, which are included merely for purposes of illustration of certain aspects and embodiments of the present invention, and are not intended to limit the invention.

EXAMPLES

Example 1

An Increase in TNF-Alpha Levels Induces FIP2 Expression and is Associated with PC2 Disruption and Loss of Polycystin Function A. An Increase in TNF-Alpha Results in Mislocalization of PC2

To explore the role of TNF-alpha in FIP2 regulation of polycystin function, the effects of TNF-alpha on the localization of PC2 in inner medullary collecting duct (IMCD) cells were first tested by immunofluorescence using an anti-PC2 antibody (96525) (FIG. 1). IMCD (ATCC catalog no. CRL-2123) cells were cultured in Dulbecco's modified Eagle's medium/F12 medium supplemented with 10% (v/v) fetal bovine serum (Invitrogen). Then, these cells were induced with TNF-alpha at a final concentration of 200 ng/ml. Immunofluorescence of the IMD cells was performed before and after 16 hours of TNF-alpha exposure.

Immunofluorescence was carried out as previously described. Li et al, Polycystin-1 and polycystin-2 regulate the cell cycle through the helix-loop-helix inhibitor Id2. Nat Cell Biol, 7(12):1202-12 (2005). Primary antibodies were used at the following dilutions: FIP2 (1:100), PC1 (1:500), PC2 (1:500), and flag (1:500). Secondary antibodies used included goat-anti-rabbit IgG-fluorescein isothiocyanate (Molecular Probes, Eugene, Oreg.) and goat-anti-mouse IgG-Texas Red (1:500 dilution; Molecular Probes). Images were captured on an inverted microscope (Axiovert 200M, Carl Zeiss, inc.) equipped with a spinning disc confocal head (Yogogawa), Argon-Krypton laser system (Prairie Technologies, Inc.), and ORCA-ER CCD camera (Hamamatsu). Images were acquired using the Metamorph software (Molecular Devices) and 3D image reconstruction was performed using the Volocity (Improvision, Inc.) software.

As shown in FIGS. 1A, B, A' and B', a comparison of IMCD cells was performed before and after TNF-alpha induction. The results show that TNF-alpha stimulation produced a loss of PC2 localization to the plasma membrane and primary cilia. In untreated IMCD cells, endogenous PC2 localized to the plasma membrane and was observed in >95% of the primary cilia (see FIGS. 1A, A'). However, cells treated with 200 ng/ml of TNF-alpha showed a striking loss of PC2 staining at the plasma membrane and cilia (observed in 100% of the cells). Instead, there was an enrichment of PC2 within perinuclear regions (see FIGS. 1B, B').

B. Confirmation of PC2 Localization by the FIP2 Inhibitor TNF-Alpha

Figure 5:
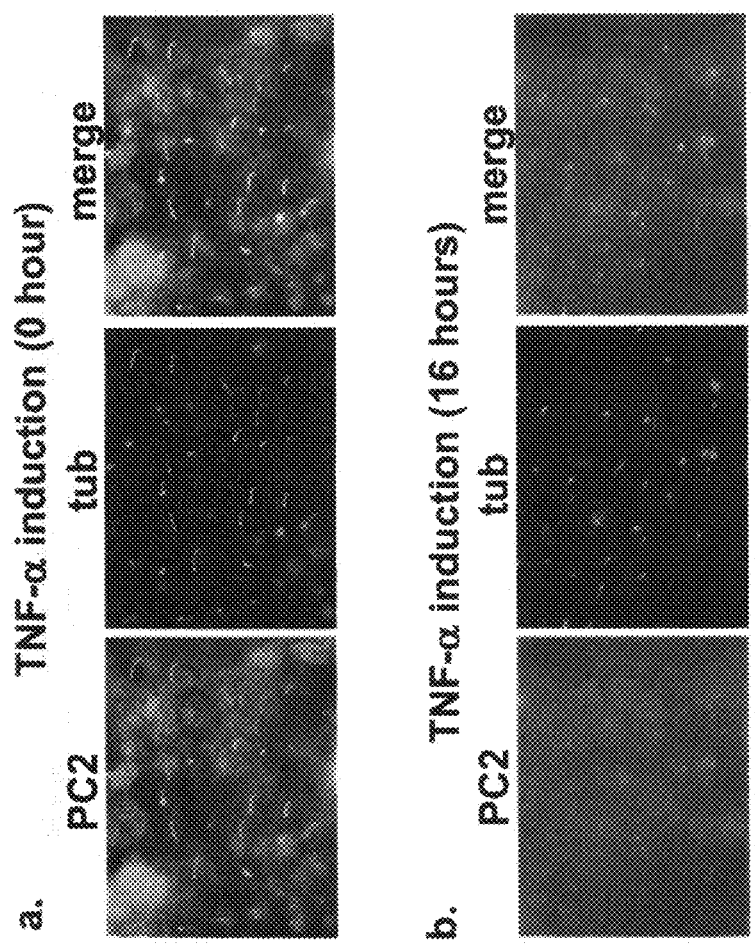
FIG. 5 shows double immunofluorescence staining of endogenous PC2 (green) and acetylated tubulin (red) before (5a) or after (5b) treatment with TNF-alpha for 16 hr, observed with confocal microscopy.

The disruption of PC2 localization by TNF-alpha was further confirmed using immunoprecipitation, western blotting, and a TUNEL Assay. Immunoprecipitation and Western blotting were performed on whole-cell lysates as previously described. Li et al, Polycystin-1 and polycystin-2 regulate the cell cycle through the helix-loop-helix inhibitor Id2. Nat Cell Biol, 7(12):1202-12 (2005). The antibodies used for Western blotting included rabbit polyclonal anti-FIP2 51, rabbit anti- PC2 polyclonal antibody 96525 50, rabbit anti-PC1 polyclonal antibody 96521, rabbit anti-Rab8 polyclonal antibody and rabbit anti-TNFR-I polyclonal antibody. Secondary antibodies used included: goat-anti-rabbit IgG-fluorescein isothiocyanate (FITC Molecular Probes, Eugene, Oreg.), goat-anti-mouse IgG-Texas Red, (1:500 dilution; Molecular Probes). For western blotting, goat-anti-rabbit IgG-horseradish peroxidase (HRP or goat-anti-mouse IgG-HRP, 1:10,000 dilution; Amersham Pharmacia Biotech) were used as secondary antibodies. As shown in FIG. 5, TNF-alpha signaling disrupted PC2 cilia localization in IMCD cells as detected by staining with the YCC2 anti-PC2 antibody. Moreover, TNF-alpha stimulation resulted in the loss of PC2 localization along the primary cilia, however, with this antibody, PC2 was still detected in the basal body regions in some of the treated cells.

Figure 6:
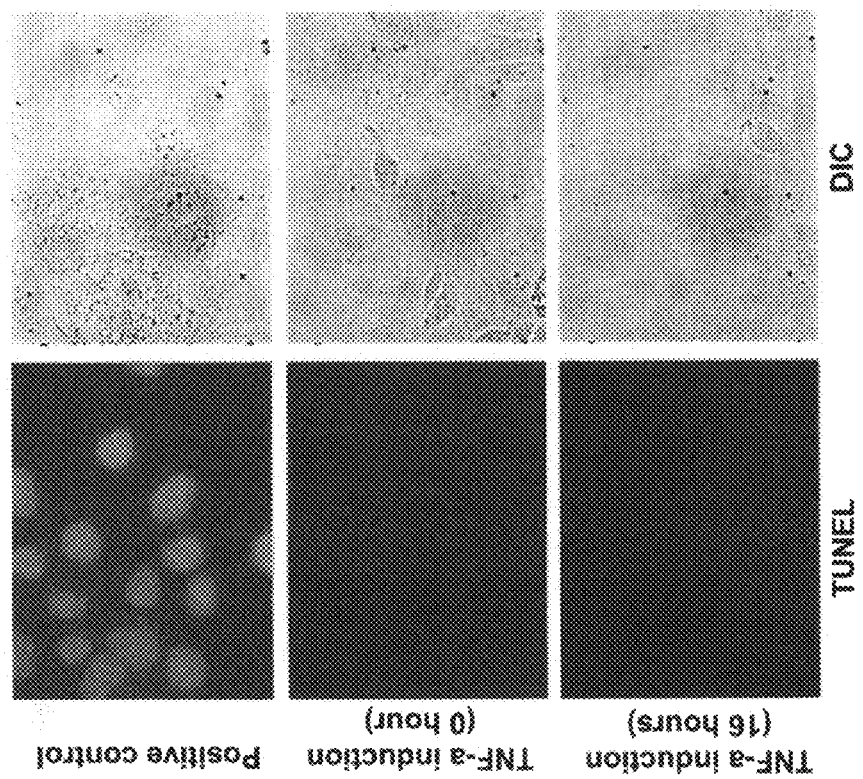
FIG. 6 shows TUNEL staining (left column) of the TNF-alpha treated IMCD cells (at 0 and 16 hours post-treatment) and under DIC (right column).

To confirm that localization of PC2 was not due to cell death, a TUNEL Assay was performed. Cells treated with or without TNF-alpha were fixed with 4% PFA. The TUNEL assay was performed using a fluorescent apoptosis-detection system (R&D systems, Minneapolis, Minn.) according to the manufacturer's instructions. Fixed cells were treated with TACS-nuclease for the positive control. As shown in FIG. 6, the loss of membrane localization of PC2 was not due to cell death, as the TNF-alpha-treated cells showed normal morphology and were negative for TUNEL staining Example 2

TNF-Alpha Promotes Cysts

A. TNF-Alpha Promotes Cyst Formation

In addition to establishing a relationship wherein TNF-alpha disrupts polycystin function, the above cellular data also provided a potential mechanism by which TNF-alpha promotes cyst formation by disrupting the normal function of PC2 via FIP2. The proposed PC2 mechanism was tested using a mouse embryonic kidney organ culture assay.

Embryonic kidneys were dissected in PBS (with calcium and magnesium) plus penicillin-streptomycin-glutamine (GiBCO, Grand Island, N.Y.) from embryos of wild type CD1 mice at E15.5, E16.5 or E17.5 and of C57BL/6 Pkd1+/− or C57BL/6 Pkd2+/− mice or their wild type counterparts at E15.5. The dissected kidneys were cultured at 37° C. in DMEM/F12 containing 2 mM L-glutamine, 10 mM Hepes, 5 µg/ml insulin, 5 µg/ml transferrin, 2.8 mM selenium, 25 ng/ml prostaglandin E1, 32 pg/ml T3 and 250 IU/ml penicillin-streptomycin. The kidneys were cultured with or without TNF-alpha (Genzyme Diagnostic, Cambridge, Mass.) at different concentrations for 48 hours and then 50 µM 8-Bromo-cyclic AMP (Sigma, St. Louis, Mo.) was added for 5 days. The cultured kidneys were then fixed with 4% paraformaldehyde (PFA) in PBS for 6 hours, washed with PBS twice for 5 minutes each, and transferred to 70% EtOH for short-term storage at room temperature or for more extended storage at 4° C. The fixed kidney samples were subsequently processed for Hematoxylin and Eosin staining following a common histology protocol.

Figure 2:
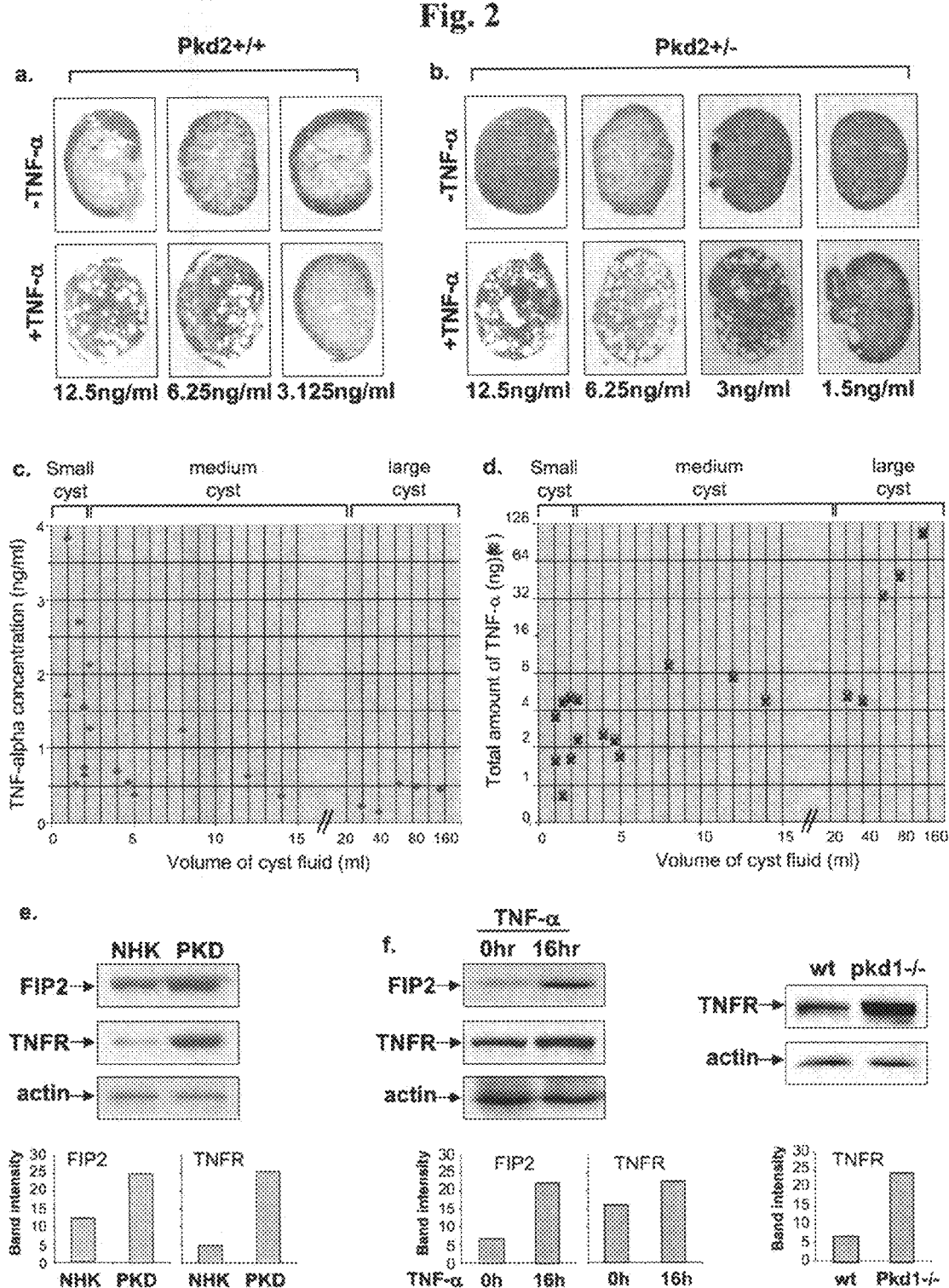
FIG. 2a-f shows that TNF-alpha treatment triggers cyst formation in wild type and Pkd+/− cultured kidneys and is present in human ADPKD cyst fluid.

This assay was utilized to demonstrate the direct effects of cAMP in CFTR/NKCC1-dependent cystic dilation. To test the effect of TNF-alpha treatment, the culture conditions were modified using E15.5 kidneys and a low concentration of cAMP, such that there was no cyst formation (0/32 kidneys observed) in the absence of TNF-alpha (see top panel FIGS. 2A and 2B). However, treatment for five days with concentrations as low as 6.25 ng/ml TNF-alpha resulted in formation of numerous cysts in the wild type embryonic kidneys (FIG. 2A; observed in 20/20 cultured kidneys treated with 6.25-12.5 ng/ml TNF-alpha). Significantly, in Pkd2+/− embryonic kidneys cyst formation occurred at TNF-alpha concentration as low as 1.5 ng/ml. (FIG. 2B). These results indicate that TNF-alpha may promote kidney cyst formation by impairing the function of PC2. Thus, in FIG. 2B, treatment with different concentrations of TNF-alpha for 5 days triggered cyst formation in Pkd2+/− cultured kidneys from E15.5 embryos. FIGS. 2A and 2B demonstrate that the TNF-alpha can promote kidney cyst formation by impairing the functioning of PC2.

B. Quantification of TNF-Alpha Concentration in Human ADPKD Cyst Fluids

To further explore the link between increased TNF-alpha levels and increased cyst formation, the concentrations of TNF-alpha in human ADPKD cyst fluids obtained from 10 patients were quantified. Cyst fluids were collected from 10 ADPKD kidneys maintained at 4° C. The fluid was cleared by centrifugation and aliquots were frozen at −20° C. The concentrations and total amounts of TNF-alpha in individual cyst fluids were measured using the DuoSet ELISA Development kit for human TNF-alpha/TNFSF1A (R&D Systems, Minneapolis, Minn.). The results for measuring cyst fluids are indicated in FIGS. 2C and D. The results indicated a significant accumulation of TNF-alpha, with concentrations in small cysts indeed reaching the ng/ml range and the highest reaching 3.8 ng/ml in the most freshly collected cyst fluid (FIG. 2C). Furthermore, there was an inverse relationship between cyst size and TNF-alpha concentration (FIG. 2D), suggesting that TNF-alpha secreted into the lumen by the cyst-lining cells might have been diluted by the large fluid volume of large cysts. However, the total amount of TNF-alpha appeared to increase with larger cyst size (FIG. 2D), indicating that TNF-alpha continuously accumulated as cysts grow. Accordingly, as the size of the cyst grows, TNF-alpha accumulates at higher concentrations, which perpetuates PC2 dislocalization and cell proliferation.

Example 3

TNF-Alpha Increases Signaling and FIP2 Levels

To test if TNF-alpha levels may induce FIP2 expression in cystic kidneys, the amount of FIP2 protein was compared between primary cultures of normal human kidney cells (NHK) and ADPKD human cyst lining cells (PKD). Immunoblot analysis of FIP2 and TNFR protein levels were also performed by comparing cultured normal human kidney (NHK) cells and ADPKD cyst lining PKD cells in FIG. 2E.

Primary cultures of ADPKD and normal human kidney (NHK) cells were generated with the assistance of the PKD Biomaterials Research Core laboratory at the University of Kansas Medical Center (KUMC). Normal regions of human kidneys, confirmed by histological examination, were collected from nephrectomy specimens removed for the treatment of renal carcinomas. ADPKD kidneys were obtained from hospitals participating in the Polycystic Kidney Research Retrieval Program with the assistance of the PKD Foundation (Kansas City, Mo.). The kidneys were packaged within ice and shipped to the laboratory overnight. A protocol for the use of discarded human tissues complies with federal regulations and was approved by the Institutional Review Board at KUMC.

Primary cell cultures were prepared as described previously. The cells were propagated in DMEM/F12 supplemented with 5% FBS, 5 µg/ml insulin, 5 µg/ml transferrin and 5 ng/ml sodium selenite (ITS) and 100 IU/ml penicillin G and 0.1 mg/ml streptomycin. Primary cultures of ADPKD and NHK cells appeared epithelial and stained with *Arachis hypogaea* and *Dolichos biflorus*, lectins that bind the collecting ducts and distal tubules. Immunoblot analysis of FIP2 and TNFR protein levels were performed as discussed above.

Mouse embryonic kidney (MEK) cells isolated from E15.5 wild-type and Pkd1 mutant mice (Pkd1−/−) were cultured at 33° C. Cells were cultured to 30%-50% confluence and transiently transfected with Fugene 6 transfection reagent (Roche, Indianapolis, Ind.) following the manufacturer's protocol. Cells were harvested for further analysis 48 hours after transfection.

As shown in FIG. 2E, there was a 1.1-fold increase of FIP2 in the PKD cells compared to that in NHK cells. This increase was slightly lower than that in TNF-alpha treated IMCD cells, where the FIP2 level was induced by 2 fold (FIG. 2F, top panel). Interestingly, the levels of TNF-alpha receptor (TNFR) also exhibited an increase (3-fold) in the cyst lining cells over NHK cells. Consistent with this, TNFR levels were increased by 35% in TNF-alpha treated IMCD cells (FIG. 2F, top panel) and 2.5-fold in Pkd1−/− mutant mouse cells, compared to wild type cells (FIG. 2F, bottom panel). This result indicates that exposure to TNF-alpha stimulates the expression of TNFR, which in turn may render the cystic epithelial cells more sensitive to TNF-alpha and increase FIP2 expression resulting in loss of polycystin function.

Example 4

PC2 Localization is FIP2-Dependent

A. TNF-Alpha Induces FIP2 Expression and Results in PC2 Disruption—Decrease in Polycystin Function RNAi specific to FIP2 was used to test if the effect of TNF-alpha on PC2 localization was FIP2-dependent. IMCD cells were transfected with siRNA specific for FIP2 to determine if FIP2 caused mislocalization of PC2 upon TNF-alpha induction. The oligo sequences used for FIP2 RNAi (Dharmacon, Chicago, Ill.) are shown in Table 1, below:

TABLE 1

List of sense and antisense sequences used.

| | | | |
|---|---|---|---|
| SEQ ID NO: 1 | #05 Sense sequence: | 5'-GCUAUGAAAGGGCGAUUUGUU |
| SEQ ID NO: 2 | #05 Antisense sequence: | 5'-PCAAAUCGCCCUUUCAUAGCUU |
| SEQ ID NO: 3 | #06 Sense sequence: | 5'-UGAGCUGCCUGACUGAGAAUU |
| SEQ ID NO: 4 | #06 Antisense sequence: | 5'-PUUCUCAGUCAGGCAGCUCAUU |
| SEQ ID NO: 5 | #07 Sense sequence: | 5'-GAAAUGCAGUGCCGACACGUU |
| SEQ ID NO: 6 | #07 Antisense sequence: | 5'-PCGUGUCGGCACUGCAUUUCUU |
| SEQ ID NO: 7 | #08 Sense sequence: | 5'-CCAUGAAGCUAAAUAAUCAUU |
| SEQ ID NO: 8 | #08 Antisense sequence: | 5'-PUGAUUAUUUAGCUUCAUGGUU |

The transfection was performed using the DharmaFECT siRNA transfection reagent (Dharmacon, Chicago, Ill.) according to the manufacturer's protocol.

In FIGS. 1C and 1D, anti-PC2 antibodies (96525 FIG. 1C; YCC2 FIG. 1D) at a concentration of 1:500 were used to determine whether FIP2 siRNA reduces or eliminates FIP2 expression to restore PC2 localization in TNF-alpha treated IMCD cells.

Figure 7:
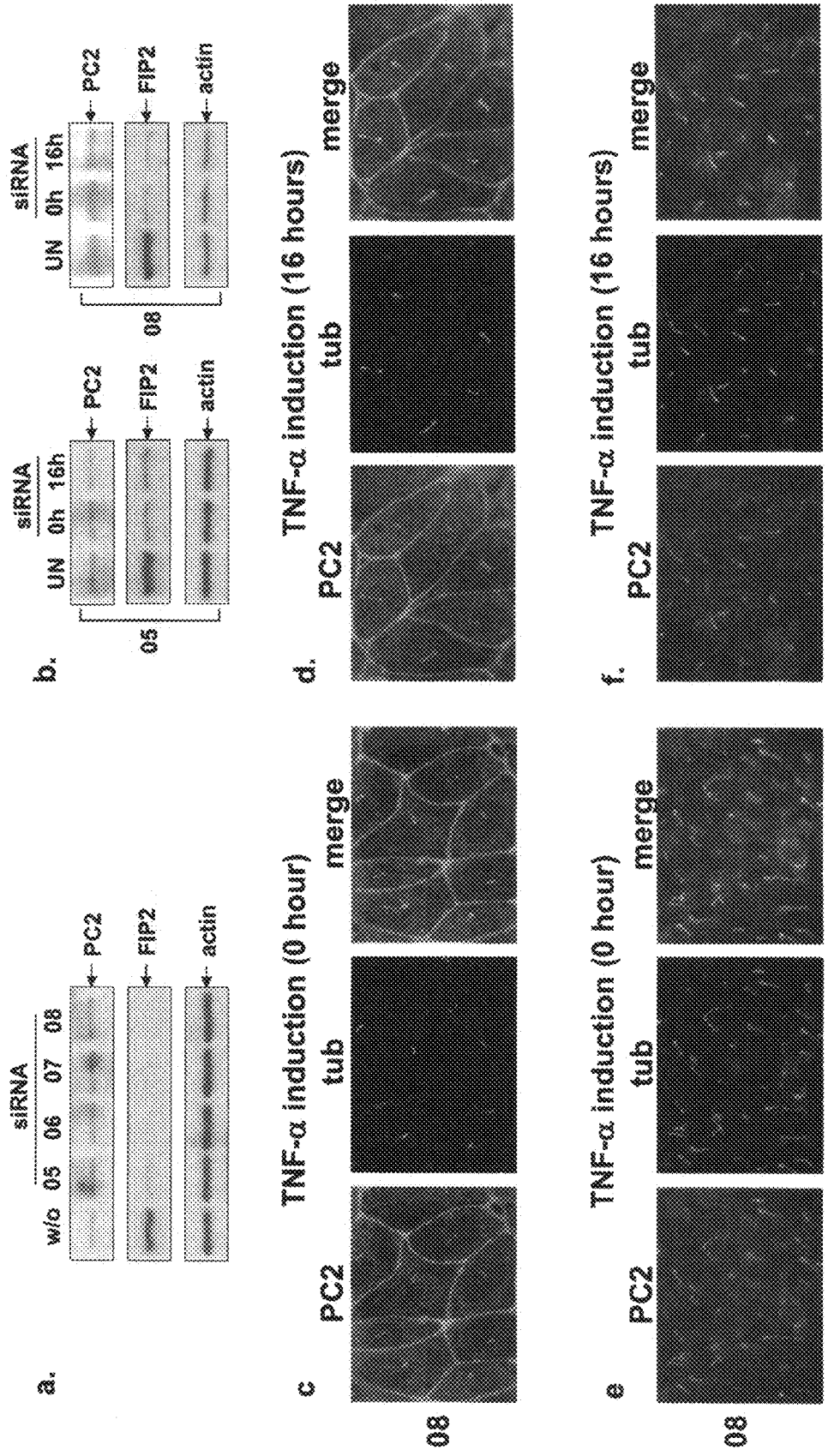
FIG. 7 shows transfection of siRNA against FIP2 into IMCD cells inhibited FIP2 expression and rescued the TNF-alpha effect on PC2 localization.

In FIG. 7A, 4 different siRNAs against FIP2 were transfected into IMCD cells. In FIG. 7B, a Western blot was performed as described above using anti-FIP2 antibody to determine FIP2 levels in IMCD cells, which were transfected with siRNA#05 (SEQ ID NO: 2) and #08 (SEQ ID NO: 8) and then treated with TNF-alpha for 16 hours. In FIGS. 7C-7F, immunostaining was performed as described above with 96525 anti-PC2 antibody or YCC2 anti-PC2 antibody at a concentration of 1:500 with IMCD cells transfected with siRNA#08 (SEQ ID NO: 8) before and after TNF-alpha induction. Transfection of siRNA against FIP2 into IMCD cells inhibited FIP2 expression and rescued the TNF-alpha effect on PC2 localization.

As shown in FIGS. 7A and 7B, FIP2 siRNA knocked down FIP2 expression by 95% and restored normal PC2 localization in TNF-alpha treated cells, as detected using either of the anti-PC2 antibodies (96525 or YCC2) (FIGS. 1C, D, 7C-F). Furthermore, over-expression of Flag-tagged FIP2 in IMCD cells by transient transfection disrupted PC2 localization to the plasma membrane, resulting in PC2 localization with FIP2 in punctuate perinuclear structures (FIGS. 1E, E'). In contrast, the neighboring untransfected cell showed the normal PC2 localization. These results indicate that siRNA specific to FIP2 rescues PC2 cilia localization despite treatment with TNF-alpha. Accordingly, induction of FIP2 downstream of TNF-alpha signaling disrupts the localization of PC2 to its normal sites of function.

Example 5

In Vitro Results Corroborated by In Vivo Testing

A. TNF-Alpha Signalling Induces FIP2 Expression and Cyst Formation In Vivo

Figure 3:
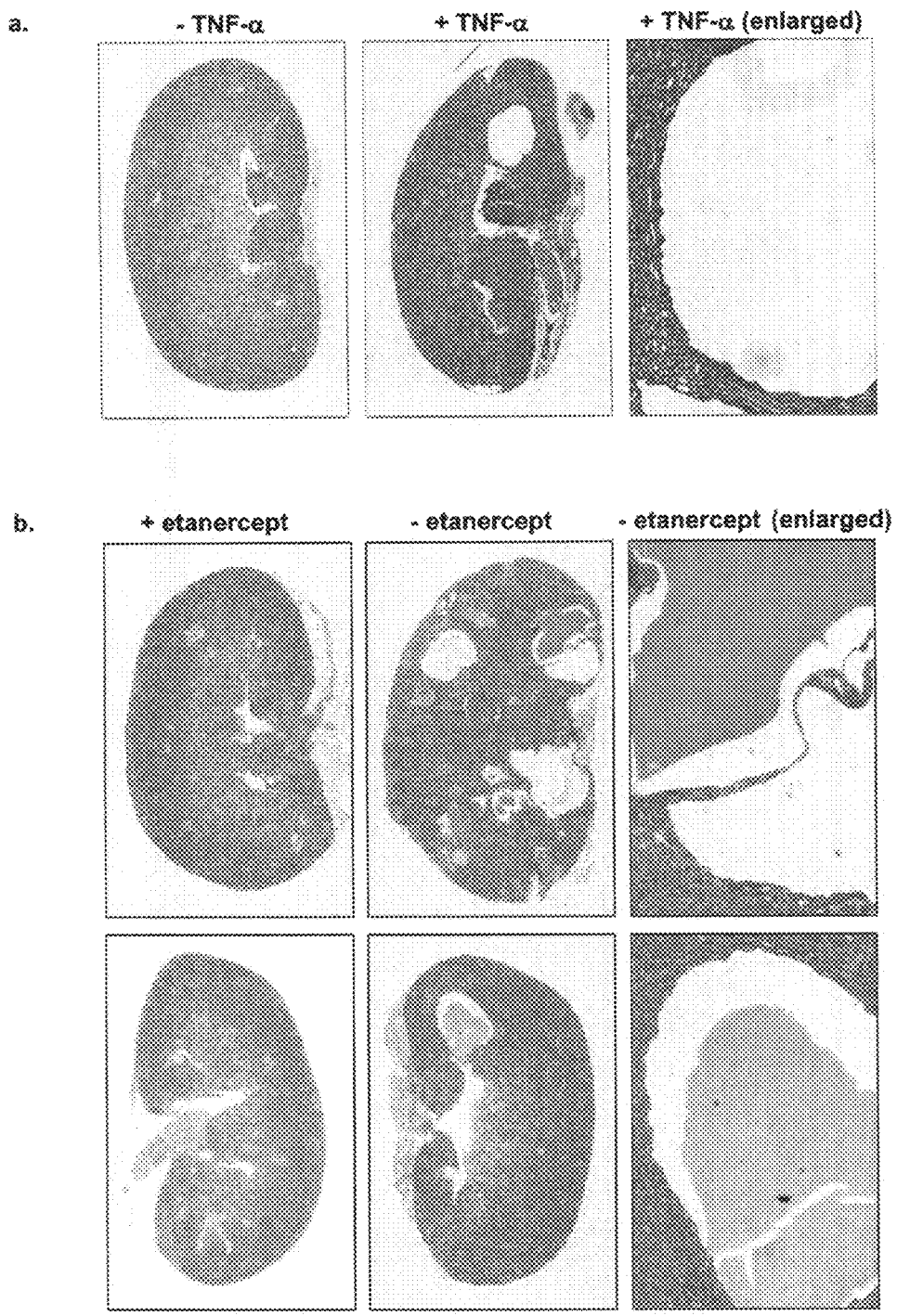
FIG. 3a shows kidney histology sections from Pkd2+/− mice injected intraperitoneally with TNF-alpha at 5 μg/mouse/week (middle and right panels) or phosphate buffered saline (PBS) (left panel).
FIG. 3b shows kidney histology sections from Pkd2+/− mice injected intraperitoneally with etanercept (left column) or PBS (middle and right columns).

The in vitro results described above indicate that TNF-alpha may be a strong physiological modifier of FIP2 that promotes the ADPKD disease phenotype at the organismal level. To test this hypothesis in vivo, 4 week old Pkd2+/− mice were directly injected intra-peritoneally with TNF-alpha (5 μg/mouse, 1 injection/wk) for 4 weeks. Pkd2 mutant mice (Pkd2-183) were kindly provided by Stephan Somlo (Yale University). For TNF-alpha (Genzyme Diagnostic, Cambridge, Mass.) treatment experiments, mice were intraperitoneally injected weekly, from week 4 (day 28) to week 8.5 (day 60), with 5 μg of TNF-alpha per mouse per week or phosphate buffered saline (PBS). 9-17 week old Pkd2+/− mice developed cysts at a frequency of 0.21. Accordingly, the natural frequency of cyst formation may be much lower in the 4 week olds. As shown in FIG. 3A, no cysts were observed in the control group (n=10), however, 4 of the 10 TNF-alpha-treated mice developed unilateral cysts. Fisher's exact test gave p=0.04, indicating that the difference between the treatment and control group is significant. This result suggests that TNF-alpha accelerates cyst development in the Pkd2+/− mouse model.

B. FIP2 Inhibitors Can Neutralize TNF-Alpha Signaling and Treat Cyst Formation

Chronic inhibition of FIP2 expression by a FIP2 inhibitor such as a TNF-alpha inhibitor may alleviate cyst formation. For the TNF-alpha inhibitor etanercept (AMGEN, Thousand Oaks, Calif.), treatment experiments, mice were intraperitoneally injected weekly, from week 8.5 (day 60) to week 18.5 (day 130), with 25 μg of etanercept per mouse per week or phosphate buffered saline (PBS).

To this end, 8-week old Pkd2+/− mice were treated with either etanercept subcutaneously administered at 25 μg/mouse/week), or phosphate buffered saline (PBS) in the control group. As shown in FIG. 3B, after 10 weeks of treatment, 25% of the control group, now 18 weeks old, developed unilateral cysts (n=16). This frequency is consistent with that reported previously (21%, n=29). Remarkably, none of etanercept-treated mice developed kidney cysts (n=14). Fisher's exact test yielded p=0.05, suggesting that neutralization of TNF-alpha and thereby FIP2 significantly reduced cyst formation in Pkd2+/− mice.

In sum, the inventors have unexpectedly shown that by modulating an agent in the TNF pathway, such as TNF-alpha or FIP2, a polycystic disease may be treated and/or it effects ameliorated.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of inhibiting or ameliorating renal cyst development in a subject with a polycystic kidney disease comprising administering to a subject in need thereof a therapeutically effective amount of a TNF-α inhibitor.

2. The method according to claim 1, wherein the polycystic kidney disease is autosomal dominant polycystic kidney disease (ADPKD) or autosomal recessive polycystic kidney disease (ARPKD).

3. The method according to claim 1, wherein the TNF-alpha inhibitor is an antibody or soluble TNF receptor fusion polypeptide that binds TNF-alpha.

4. The method according to claim 3, wherein the TNF-alpha inhibitor is selected from the group consisting of Cyto-Fab (a polyclonal ovine anti TNF-alpha antibody Fab fragment), certolizumab pegol (a PEGylated Fab' fragment of a humanized anti-TNF-alpha monoclonal antibody), adalimumab (a recombinant human IgG$_1$ monoclonal anti TNF-alpha antibody), etanercept (a dimeric fusion protein consisting of the extracellular ligand-binding domain of the human 75 kd (p75) TNF receptor linked to the Fc portion of human IgG$_1$), infliximab (a human-mouse chimeric IgG$_1$κ anti-TNF-alpha monoclonal antibody), onercept (a recombinant human soluble p55 TNF binding protein), VT-346 (a 43-kd secreted glycoprotein that is a human TNF-alpha inhibitor), golimumab (a fully human anti-TNF-alpha antibody), CYT-6091 (a nanotherapeutic in which TNF-alpha is covalently linked onto the surface of 30 nm particles of pegylated colloidal gold), Dom-0200 (an anti-TNF-alpha human domain antibody), ABX/0401 (a sc humanized anti-TNF-alpha monoclonal antibody), XPro-1595 (a dominant negative protein variant of TNF-alpha that selectively inhibits soluble TNF-alpha), anti-TNF-alpha, ABX/0402 (a humanized anti-TNF-alpha monoclonal antibody), TNF-alpha kinoid (a kinoid vaccine, which induces synthesis of polyclonal antibodies against TNF-alpha), CYT007-TNFQb (a vaccine designed to elicit anti-TNF-alpha antibodies), ESBA-105 (a fully humanized fragment of the VH/VL domains that inhibits TNF-alpha), Dom-0100 (an anti-TNFR1 human domain antibody), PN-0615 (an anti-TNF-alpha human monoclonal antibody), and combinations thereof.

5. The method according to claim 4, wherein the TNF-alpha inhibitor is etanercept.

6. The method according to claim 1, wherein the TNF-alpha inhibitor regulates the activity of tissue necrosis factor (TNF)-alpha.

7. A method of inhibiting or ameliorating renal cyst development in a subject with a polycystic kidney disease (PKD) comprising administering to a subject in need thereof an amount of a TNF-alpha inhibitor comprising etanercept that is sufficient to inhibit or ameliorate an effect of PKD.

* * * * *

```
                           SEQUENCE LISTING

<160> NUMBER OF SEQ ID NOS: 8

<210> SEQ ID NO 1
<211> LENGTH: 21
<212> TYPE: RNA
<213> ORGANISM: Artificial
<220> FEATURE:
<223> OTHER INFORMATION: Synthetic Construct

<400> SEQUENCE: 1
gcuaugaaag ggcgauuugu u                                                 21

<210> SEQ ID NO 2
<211> LENGTH: 21
<212> TYPE: RNA
<213> ORGANISM: Artificial
<220> FEATURE:
<223> OTHER INFORMATION: Synthetic Construct

<400> SEQUENCE: 2
caaaucgccc uuucauagcu u                                                 21

<210> SEQ ID NO 3
<211> LENGTH: 21
<212> TYPE: RNA
<213> ORGANISM: Artificial
<220> FEATURE:
<223> OTHER INFORMATION: Synthetic Construct

<400> SEQUENCE: 3
ugagcugccu gacugagaau u                                                 21

<210> SEQ ID NO 4
<211> LENGTH: 21
<212> TYPE: RNA
<213> ORGANISM: Artificial
<220> FEATURE:
<223> OTHER INFORMATION: Synthetic Construct

<400> SEQUENCE: 4
uucucaguca ggcagcucau u                                                 21

<210> SEQ ID NO 5
```

```
<211> LENGTH: 21
<212> TYPE: RNA
<213> ORGANISM: Artificial
<220> FEATURE:
<223> OTHER INFORMATION: Synthetic Construct

<400> SEQUENCE: 5
gaaaugcagu gccgacacgu u                                              21

<210> SEQ ID NO 6
<211> LENGTH: 21
<212> TYPE: RNA
<213> ORGANISM: Artificial
<220> FEATURE:
<223> OTHER INFORMATION: Synthetic Construct

<400> SEQUENCE: 6
cgugucggca cugcauuucu u                                              21

<210> SEQ ID NO 7
<211> LENGTH: 21
<212> TYPE: RNA
<213> ORGANISM: Artificial
<220> FEATURE:
<223> OTHER INFORMATION: Synthetic Construct

<400> SEQUENCE: 7
ccaugaagcu aaauaaucau u                                              21

<210> SEQ ID NO 8
<211> LENGTH: 21
<212> TYPE: RNA
<213> ORGANISM: Artificial
<220> FEATURE:
<223> OTHER INFORMATION: Synthetic Construct

<400> SEQUENCE: 8
ugauuauuua gcuucauggu u                                              21
```